United States Patent
Miyazaki et al.

(10) Patent No.: US 8,491,286 B2
(45) Date of Patent: Jul. 23, 2013

(54) TUBE UNIT, CONTROL UNIT, AND MICROPUMP

(75) Inventors: Hajime Miyazaki, Matsumoto (JP); Kazuo Kawasumi, Chino (JP)

(73) Assignee: Seiko Epson Corporation (JP)

( * ) Notice: Subject to any disclaimer, the term of this patent is extended or adjusted under 35 U.S.C. 154(b) by 412 days.

(21) Appl. No.: 12/623,652

(22) Filed: Nov. 23, 2009

(65) Prior Publication Data
US 2010/0143168 A1 Jun. 10, 2010

(30) Foreign Application Priority Data
Dec. 5, 2008 (JP) .................................. 2008-310593

(51) Int. Cl.
*F04B 43/12* (2006.01)

(52) U.S. Cl.
USPC .......................................... 417/477.2; 417/474

(58) Field of Classification Search
USPC ......... 417/474–477.14; 604/153; 310/323.02, 310/323.04, 323.16, 323.17, 366
See application file for complete search history.

(56) References Cited

U.S. PATENT DOCUMENTS

| | | | |
|---|---|---|---|
| 3,574,883 | A | 4/1971 | Brittain et al. |
| 3,630,647 | A | 12/1971 | Kochlin |
| 4,155,362 | A | 5/1979 | Jess |
| 4,187,057 | A | 2/1980 | Xanthopoulos |
| 4,607,764 | A | 8/1986 | Christine |
| 4,648,812 | A | 3/1987 | Kobayashi et al. |
| 4,735,558 | A | 4/1988 | Keinholz et al. |

(Continued)

FOREIGN PATENT DOCUMENTS

| | | |
|---|---|---|
| EP | 0 570 134 | 11/1993 |
| JP | 54-103290 | 8/1979 |

(Continued)

OTHER PUBLICATIONS

Extended European Search Report for application No. 09171345.3 (6 pages), dated Nov. 19, 2010.

*Primary Examiner* — Peter J Bertheaud
*Assistant Examiner* — Dnyanesh Kasture
(74) *Attorney, Agent, or Firm* — Harness, Dickey & Pierce, P.L.C.

(57) ABSTRACT

A micropump includes: a tube unit which includes a tube having elasticity and a circular-arc-shaped part, a plurality of fingers extending in radial directions from the circular-arc center of the circular-arc shape of the tube, and a tube guide frame which holds the tube and the plural fingers; a control unit which includes a cam for sequentially pressing the plural fingers from the fluid flow-in side to the fluid flow-out side of the tube, a rotor for giving rotational force to the cam, and an oscillator having a piezoelectric element and a projection disposed at an end in the longitudinal direction to contact the rotor; a reservoir which communicates with a flow inlet portion of the tube; a control circuit unit which inputs a drive signal to the piezoelectric element; and a power source which supplies power to the control circuit unit, wherein the tube unit is attachable to and detachable from the control unit substantially in the horizontal direction with respect to the rotation flat plane of the cam, and the oscillator is oscillated by applying alternating voltage to the piezoelectric element, rotational force is repeatedly given to the rotor from the projection, the plural fingers are sequentially pressed by the cam from the flow-in side to the flow-out side of fluid, and fluid is transported by repeating closure and open of the tube.

18 Claims, 13 Drawing Sheets

U.S. PATENT DOCUMENTS

| | | |
|---|---|---|
| 4,869,646 A | 9/1989 | Gordon et al. |
| 4,909,710 A | 3/1990 | Kaplan et al. |
| 4,954,046 A | 9/1990 | Irvin et al. |
| 5,049,047 A | 9/1991 | Polaschegg et al. |
| 5,083,908 A | 1/1992 | Gagnebin et al. |
| 5,249,937 A | 10/1993 | Aubert |
| 5,318,413 A | 6/1994 | Bertoncini |
| 5,342,180 A | 8/1994 | Daoud |
| 5,531,697 A | 7/1996 | Olsen et al. |
| 5,531,698 A | 7/1996 | Olsen |
| 5,575,631 A | 11/1996 | Jester |
| 5,647,854 A | 7/1997 | Olsen et al. |
| 5,658,252 A | 8/1997 | Johnson |
| 5,683,233 A | 11/1997 | Moubayed et al. |
| 5,791,881 A | 8/1998 | Moubayed et al. |
| 5,817,116 A | 10/1998 | Takahashi et al. |
| 5,924,852 A | 7/1999 | Moubayed et al. |
| 6,030,190 A | 2/2000 | Kammerer |
| 6,106,249 A | 8/2000 | Barak |
| 6,123,686 A | 9/2000 | Olsen et al. |
| 6,164,921 A | 12/2000 | Moubayed et al. |
| 6,253,968 B1 | 7/2001 | Van Dijk et al. |
| 6,371,732 B1 | 4/2002 | Moubayed et al. |
| 6,558,347 B1 | 5/2003 | Jhuboo et al. |
| 6,749,587 B2 | 6/2004 | Flaherty |
| 6,872,058 B2 | 3/2005 | Doig |
| 6,918,748 B2 * | 7/2005 | Miyazawa ............... 417/410.1 |
| 7,036,751 B1 | 5/2006 | Lund et al. |
| 7,059,840 B2 | 6/2006 | Corwin et al. |
| 7,078,847 B2 * | 7/2006 | Miyazawa et al. ....... 310/323.02 |
| 7,116,037 B2 * | 10/2006 | Moteki et al. ............ 310/323.02 |
| 7,238,010 B2 | 7/2007 | Hershberger et al. |
| 7,556,481 B2 | 7/2009 | Moubayed |
| 7,632,079 B2 | 12/2009 | Hershberger et al. |
| 7,762,795 B2 | 7/2010 | Moubayed |
| 7,963,690 B2 | 6/2011 | Thompson et al. |
| 8,152,498 B2 | 4/2012 | Bunoz |
| 2004/0116862 A1 | 6/2004 | Ray |
| 2004/0199118 A1 | 10/2004 | Christenson et al. |
| 2004/0234401 A1 | 11/2004 | Banister |
| 2006/0029505 A1 | 2/2006 | Gibson et al. |
| 2006/0073048 A1 | 4/2006 | Malackowski |
| 2006/0253086 A1 | 11/2006 | Moberg et al. |
| 2007/0154336 A1 | 7/2007 | Miyazaki et al. |
| 2007/0217932 A1 | 9/2007 | Voyeux et al. |
| 2007/0231205 A1 | 10/2007 | Williams et al. |
| 2008/0051709 A1 | 2/2008 | Mounce et al. |
| 2008/0065016 A1 | 3/2008 | Peterson et al. |
| 2008/0101967 A1 | 5/2008 | Moubayed |
| 2008/0101968 A1 | 5/2008 | Moubayed |
| 2008/0138218 A1 * | 6/2008 | Miyazaki et al. .......... 417/410.3 |
| 2008/0138222 A1 | 6/2008 | Miyazaki et al. |
| 2008/0304982 A1 | 12/2008 | Miyazaki et al. |
| 2009/0060755 A1 | 3/2009 | Miyazaki |
| 2009/0196766 A1 | 8/2009 | Detering |
| 2009/0196776 A1 | 8/2009 | Moubayed |
| 2009/0208350 A1 | 8/2009 | Miyazaki et al. |
| 2009/0240201 A1 | 9/2009 | Rotem et al. |
| 2009/0240210 A1 | 9/2009 | Walton et al. |
| 2009/0312708 A1 | 12/2009 | Miyazaki et al. |
| 2010/0021315 A1 | 1/2010 | Wolff |
| 2010/0047099 A1 | 2/2010 | Miyazaki et al. |
| 2010/0074781 A1 | 3/2010 | Miyazaki et al. |
| 2010/0080720 A1 | 4/2010 | Miyazaki et al. |
| 2010/0121306 A1 | 5/2010 | Yodfat et al. |
| 2010/0143168 A1 | 6/2010 | Miyazaki et al. |
| 2010/0296955 A1 | 11/2010 | Wolff |
| 2011/0002801 A1 | 1/2011 | Miyazaki et al. |
| 2011/0186143 A1 | 8/2011 | Miyazaki et al. |
| 2011/0186598 A1 | 8/2011 | Thompson et al. |
| 2011/0186599 A1 | 8/2011 | Thompson et al. |
| 2011/0305588 A1 | 12/2011 | Miyazaki et al. |
| 2012/0027624 A1 | 2/2012 | Miyazaki et al. |

FOREIGN PATENT DOCUMENTS

| | | |
|---|---|---|
| JP | 62-258178 | 11/1987 |
| JP | 63-83477 | 6/1988 |
| JP | 02-280763 | 11/1990 |
| JP | 05-168709 | 7/1993 |
| JP | 05-314607 | 11/1993 |
| JP | 6-21488 | 6/1994 |
| JP | 07-059853 | 3/1995 |
| JP | 09-262283 | 10/1997 |
| JP | 09-291885 | 11/1997 |
| JP | 10-028731 | 2/1998 |
| JP | 10-193651 | 7/1998 |
| JP | 3177742 | 4/2001 |
| JP | 2001-515557 | 9/2001 |
| JP | 2004-532670 | 10/2004 |
| JP | 2005-046632 | 2/2005 |
| JP | 2005-168958 | 6/2005 |
| JP | 2005-337212 | 12/2005 |
| JP | 2005-351131 | 12/2005 |
| JP | 2006-034845 | 2/2006 |
| JP | 2006-242116 | 9/2006 |
| JP | 2006-314346 | 11/2006 |
| JP | 2007-275548 | 10/2007 |
| JP | 2008-136525 | 6/2008 |
| JP | 2008-161669 | 7/2008 |
| JP | 2008-202602 | 9/2008 |
| JP | 2008-202603 | 9/2008 |
| WO | WO97/34084 | 9/1997 |

* cited by examiner

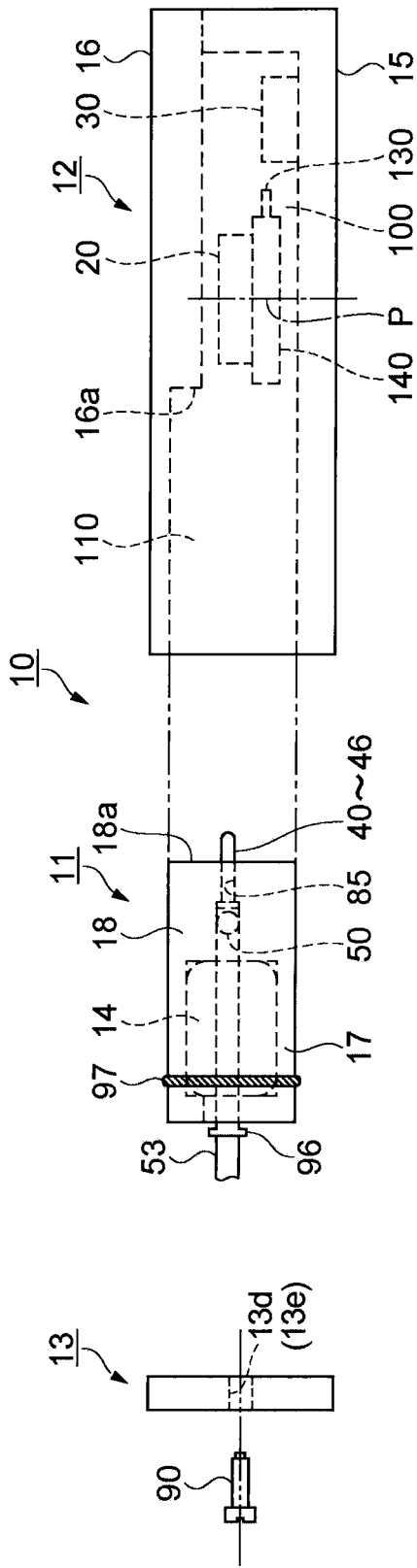

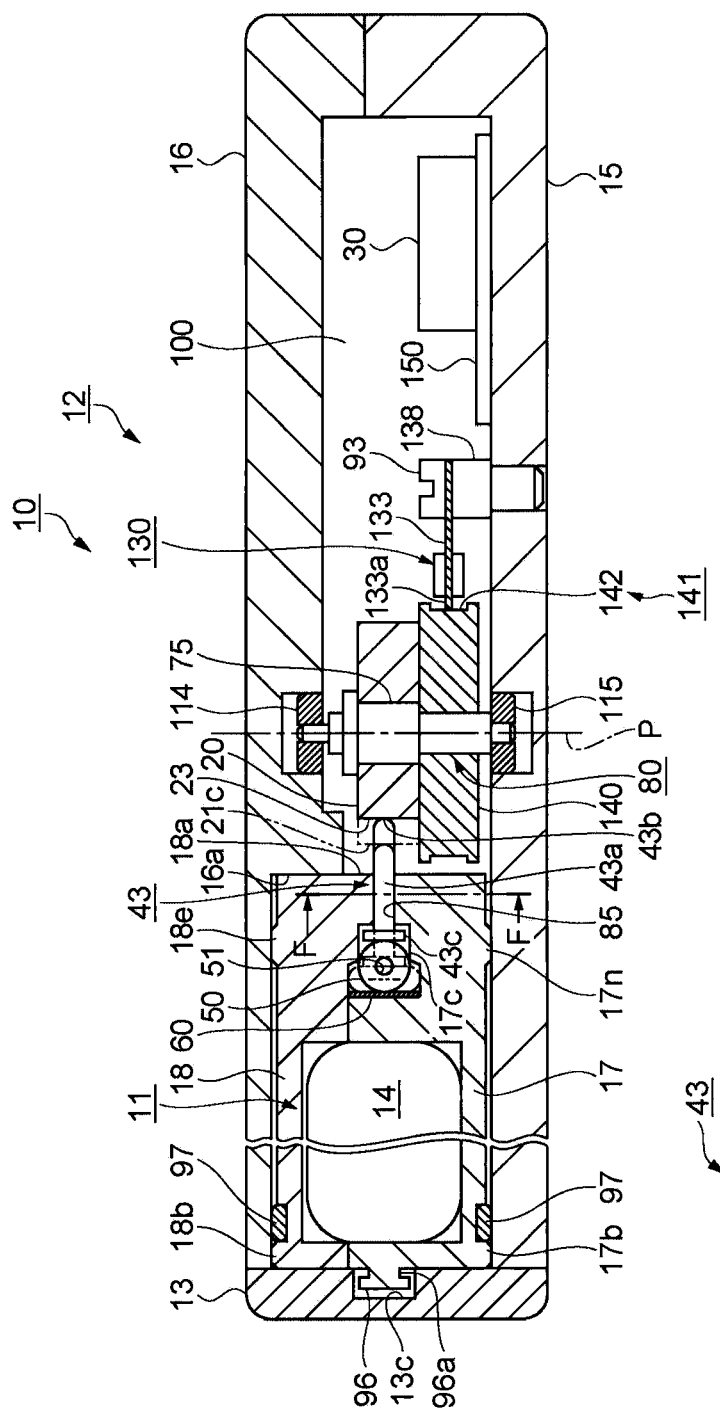
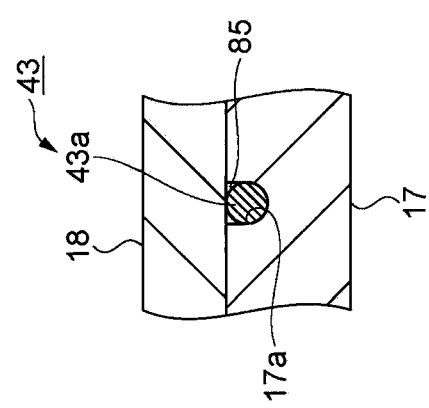
FIG. 6A
FIG. 6B

TUBE UNIT, CONTROL UNIT, AND MICROPUMP

BACKGROUND

1. Technical Field

The present invention relates to a tube unit, a control unit, and a micropump including the tube unit and the control unit both of which are attachable to and detachable from the micropump.

2. Related Art

A wriggle type pump is known as a device for transporting liquid at low speed. An example of the wriggle type pump includes a step motor as a drive source to rotate a rotor having a plurality of rollers. This rotor rotates along a flexible tube while turning the plural rollers to suck and discharge liquid (for example, see Japanese Patent No. 3177742).

This pump is produced by stacking a motor module having a step motor, and a pump module having plural rollers, a motor, and a tube.

According to the wriggle type pump disclosed in Japanese Patent No. 3177742, the tube is constantly closed by the rollers after manufacture. Thus, when the period from manufacture (assembly) until use is long, the restoration force of the tube decreases. In this case, sufficient liquid delivery accuracy cannot be secured.

Moreover, the pump produced by stacking the motor module and the pump module according to Japanese Patent No. 3177742 is difficult to reduce the thickness of the structure.

A miniaturized step motor can generate only small drive torque, and thus rotational torque of the rotor needs to be increased by using a speed reduction mechanism (speed reduction gear mechanism) having a large reduction ratio. Consequently, when a multistep reduction gear mechanism is used for this purpose, the size of the pump and the loss by the speed reduction increase.

Moreover, pinion and gear which engage with each other for attaching the stacked pump module and the motor module come to overlap with each other when the tooth phases do not agree with each other. In this case, the pinion and gear are broken.

Furthermore, it is known that the step motor generates electromagnetic noise. Thus, adverse effect may be given to peripheral devices, or the step motor may be affected by electromagnetic noise of the peripheral devices.

SUMMARY

It is an advantage of some aspects of the invention to provide a technology for solving at least a part of the problems described above, and the invention can be embodied as the following embodiments and aspects.

First Aspect

A first aspect of the invention is directed to a micropump which includes: a tube unit which contains a tube having elasticity and a circular-arc-shaped part, a plurality of fingers extending in radial directions from the circular-arc center of the circular-arc shape of the tube, and a tube guide frame which holds the tube and the plural fingers; a control unit which includes a cam for sequentially pressing the plural fingers from the fluid flow-in side to the fluid flow-out side of the tube, a rotor for giving rotational force to the cam, and an oscillator having a piezoelectric element and a projection disposed at an end in the longitudinal direction to contact the rotor; a reservoir which communicates with a flow inlet portion of the tube; a control circuit unit which inputs a drive signal to the piezoelectric element; and a power source which supplies power to the control circuit unit. The tube unit is attachable to and detachable from the control unit substantially in the horizontal direction with respect to the rotation flat plane of the cam. The oscillator is oscillated by applying alternating voltage to the piezoelectric element, rotational force is repeatedly given to the rotor from the projection, the plural fingers are sequentially pressed by the cam from the flow-in side to the flow-out side of fluid, and fluid is transported by repeating closure and open of the tube.

When the tube is continuously closed for a long period, delivery accuracy may decrease due to deterioration of restoration of the tube. According to this aspect of the invention, however, the tube unit is separable from the control unit having the cam which presses the plural fingers to close the tube. Thus, the tube is kept opened while only the tube unit is attached. Accordingly, decrease in delivery accuracy due to deterioration of restoration caused by continuous closure of the tube can be prevented, and desired delivery accuracy can be maintained.

Deterioration of the restoration of the tube may also decrease by repeating closure and open of the tube for a long period. In this case, replacement of the tube is necessary. According to this structure, the tube unit including the tube can be easily replaced after use for a certain period.

The micropump in this aspect of the invention has a structure which rotates the rotor by using the oscillator as the rotation drive source of the cam. Since the rotor driven by the oscillator has large rotation torque as will be described in detail in the following embodiments, the structure can be simplified requiring neither speed reduction gear mechanism nor coupling mechanism between the motor module and the pump module included in the related art.

The tube unit and the control unit are attached substantially in the horizontal direction with respect to the rotation flat plane of the cam. Thus, the thickness of the structure can be made smaller than the stacking structure in the related art.

The tube unit is attachable to and detachable from the control unit. Thus, running cost can be reduced by using the tube unit which a low cost and includes the tube directly contacting liquid medicine or the like as disposable component, and by repeatedly using the control unit which is a higher cost than that of the tube unit.

When the tube unit is inserted into the control unit in the horizontal direction, the fingers are brought into tube pressing condition. Thus, the coupling mechanism disposed between the motor module and the pump module included in the related art is not required, and simplification of the structure and assembly easiness can be improved.

The oscillator oscillates to rotate the rotor when alternating voltage is applied to the piezoelectric element. Thus, electromagnetic noise is not generated, and adverse effect is not given to the peripheral devices. Moreover, electromagnetic noise is not given to the oscillator from the peripheral devices. Accordingly, risks produced by electromagnetic noise can be prevented particularly in medical treatment.

Second Aspect

A second aspect of the invention is directed to the micropump of the above aspect, wherein the tube unit is inserted into a space formed in the control unit.

According to this structure, the outer periphery of the control unit has the case function. Thus, no case for accommodating the tube unit and the control unit is required, and simplification of the structure and further reduction of the thickness can be achieved.

Third Aspect

A third aspect of the invention is directed to the micropump of the above aspects, wherein: the rotor is disk-shaped; and the projection is disposed in such a position as to contact the outer circumferential side surface of the rotor.

According to the micropump of this aspect, the rotor is rotated by contact between the projection of the oscillator and the outer circumferential surface of the rotor. In this structure, the oscillation of the oscillator can be converted into rotation with high efficiency, and the rotation torque of the rotor obtained when the oscillator is oscillated under the same condition increases by bringing the oscillator into contact with the rotor having larger diameter. Thus, stable operation can be continued.

Fourth Aspect

A fourth aspect of the invention is directed to the micropump of the above aspects, wherein: the rotor is ring-shaped; and the projection is disposed in such a position as to contact the ring-shaped inner circumferential side surface of the rotor.

According to this structure, the oscillator is located inside from the outside diameter of the rotor. Thus, the size of the micropump can be reduced.

Fifth Aspect

A fifth aspect of the invention is directed to the micropump of the above aspects, wherein: the rotor is provided inside a ring-shaped concave formed on one flat surface of the cam; and the projection is disposed in such a position as to contact the inner circumferential side surface of the concave.

According to this structure, the rotor and the cam become one body. In this case, the structure becomes more simplified, and the size can be further reduced.

Sixth Aspect

A sixth aspect of the invention is directed to the micropump of the above aspects, wherein the control circuit unit, the oscillator, and the cam are dispersed at positions not overlapping with one another on a flat plane.

According to this structure, the control circuit unit, the oscillator, and the cam do not overlap with one another in a flat plane. Thus, the thickness of the control unit can be reduced, contributing to further decrease in the thickness of the micropump.

Seventh Aspect

A seventh aspect of the invention is directed to the micropump of the above aspects which further includes a speed reduction mechanism or a speed increase mechanism between the rotor and the cam.

By providing the speed reduction mechanism or speed increase mechanism, the rotation speed of the cam can be varied while keeping the rotation speed of the rotor constant. Thus, the flow amount of fluid can be appropriately controlled.

Moreover, the rotation torque of the cam can be increased in the structure including the speed reduction mechanism. Thus, stable operation can be achieved even when load produced by pressing of the tube increases.

Eighth Aspect

An eighth aspect of the invention is directed to the micropump of the above aspects, wherein the tube guide frame has a tube guide groove into which the tube is inserted, and a tube holding portion which holds the tube in the tube guide groove.

The micropump transports fluid by repeating closure and open of the tube by the plural fingers. Thus, the position of the tube needs to be accurately regulated to determine the range of the tube pressed by the fingers.

The position in the major part of the tube in the flat surface direction can be regulated by the tube guide groove, and the accurate position of the tube can be regulated by holding the range of the tube pressed by the fingers using the tube holding portion.

Ninth Aspect

A ninth aspect of the invention is directed to the micropump of the above aspects, wherein a guide portion which locates the center of the circular-arc shape of the tube and the rotation center of the cam substantially at the same position at the time of attachment of the tube unit to the control unit is provided on each side surface of the tube unit and the control unit opposed to each other.

According to the micropump in this aspect of the invention, the fingers are pressed by the rotation of the cam to close the tube. Thus, the circular-arc center of the circular-arc shape of the tube and the rotation center of the cam need to agree with each other.

By providing the guide portions on the respective side surfaces of the tube unit and the control unit opposed to each other, the center of the circular-arc shape of the tube and the rotation center of the cam can be disposed at the same position at the time of attachment of the tube unit to the control unit by the contact between the respective guide portions. Thus, all of the plural fingers can securely close the tube without using a dedicated position regulating member.

Tenth Aspect

A tenth aspect of the invention is directed to the micropump of the above aspects, wherein a detection unit which detects that the center of the circular-arc shape of the tube and the rotation center of the cam are located substantially at the same position at the time of attachment of the tube unit to the control unit is provided between the tube unit and the control unit.

According to this structure, the oscillator becomes operable when the detection unit detects the agreement between the circular-arc center of the circular-arc shape of the tube and the rotation center of the cam. In this case, all of the plural fingers can provide the same level of closure during operation. Thus, desired flow amount of fluid can be delivered per unit time.

Eleventh Aspect

An eleventh aspect of the invention is directed to the micropump of the above aspects which further includes: a cover member for fixing the tube unit to the control unit; and an elastic member which biases the tube unit to the control unit such that the center of the circular-arc shape of the tube and the rotation center of the cam can be located substantially at the same position.

When the tube unit is fixed to the control unit by using the cover member, a clearance in the horizontal direction may be produced between the tube unit and the control unit due to variances in sizes of the components. In this case, there is a possibility that the tube cannot be closed by the fingers.

According to this structure, the guide portion of the tube unit is securely brought into contact with the guide portion of the control unit by biasing the tube unit toward the control unit using the elastic member such that the circular-arc center of the circular-arc shape of the tube and the rotation center of the cam agree with each other. By this method, each of the plural fingers can securely close the tube.

Twelfth Aspect

A twelfth aspect of the invention is directed to the micropump of the above aspects, wherein the biasing force of the elastic member is larger than the tube pressing force of the plural fingers.

According to this structure, the tube unit (i.e., tube) does not move away from the fingers due to the pressing force of the fingers when the fingers press the tube. Thus, the tube can be securely closed.

Thirteenth Aspect

A thirteenth aspect of the invention is directed to the micropump of the above aspects which further includes: a tube regulating wall which regulates shift of the tube caused by the press of the plural fingers in the tube guide frame; and an elastic member disposed between the tube and the tube regulating wall.

According to this structure, excessive pressing force of the fingers is absorbed by the elastic member when the tube is pressed by the fingers. By this method, the durability of the tube becomes higher than that of the structure directly pressing the tube against the tube guide wall.

More preferable effect can be provided when the elastic member is made of material having small frictional coefficient.

Fourteenth Aspect

A fourteenth aspect of the invention is directed to the micropump of the above aspects, wherein a part or the entire area of the outer peripheries of the tube unit and the control unit is transparent.

When the outer peripheries of the tube unit and the control unit are transparent, the inside components and the engagement relations and drive conditions of the components can be visually recognized. Thus, whether the respective components are in the normal condition, where the faulty portion exists, and others can be detected. When the reservoir is accommodated in the tube unit, the liquid quantity contained in the reservoir can be visually checked.

The transparent area may be provided only in the area desired to be visually recognized.

Fifteenth Aspect

A fifteenth aspect of the invention is directed to the micropump of the above aspects, wherein either one or both of the power source and the reservoir are accommodated in the tube unit.

After repeating closure and open for a long period, deterioration of the tube may be caused. It is thus preferable that the tube is replaced after operation for a certain period. When a compact type button battery or the like is used as the power source, the battery capacity may become insufficient during use. However, insufficiency of the battery capacity during use period can be prevented by replacing both the tube and the battery as the tube unit at the time of replacement of the tube after long-term use.

When the battery is provided outside the micropump, long lead and battery case are required for connection. According to this aspect of the invention, these parts are not needed.

Sixteenth Aspect

A sixteenth aspect of the invention is directed to the micropump of the above aspects, wherein the power source and the reservoir are attachable to and detachable from the tube unit.

There is a possibility that liquid medicine stored in the reservoir becomes insufficient during use of the micropump. According to this structure, the reservoir is detachable from the tube unit (i.e., from the tube). Thus, the micropump can be used for a long period by connecting the reservoir containing liquid medicine to the tube.

When the battery is attachable to and detachable from the tube unit, the battery can be independently replaced. Thus, the micropump can be used for a long period.

Seventeenth Aspect

A seventeenth aspect of the invention is directed to the micropump of the above aspects, wherein the reservoir has a port for introducing fluid into the reservoir or sealing fluid.

In this case, the port can be constituted by a septum or the like.

By providing the septum on the reservoir, additional fluid can be easily injected into the reservoir with the reservoir connected to the tube.

Eighteenth Aspect

An eighteenth aspect of the invention is directed to the micropump of the above aspects which further includes an air vent filter which blocks passage of bubbles at a communicating portion between the reservoir and the tube.

Air dissolved in liquid contained in the reservoir gathers to become bubbles with elapse of time in some cases. When fluid is medicine to be injected into a living body, liquid containing bubbles may cause serious effect which cannot be overlooked.

When the air bent filter for transmitting liquid and blocking passage of bubbles is provided at the communicating portion between the reservoir and the tube, entrance of bubbles into the living body can be prevented. Thus, safety level increases.

Nineteenth Aspect

A nineteenth aspect of the invention is directed to a control unit attachable to and detachable from the tube unit included in the micropump of the above aspects, the control unit including: a cam which sequentially presses a plurality of fingers from the fluid flow-in side to the fluid flow-out side of a tube having elasticity and a circular-arc-shaped part, the plural fingers extending in the radial directions from the center of the circular-arc shape of the tube; a rotor which gives rotational force to the cam; and an oscillator having a piezoelectric element and a projection disposed at an end in the longitudinal direction to contact the rotor.

The control unit includes elements associated with operation such as the oscillator, the rotor, the cam, and the control circuit unit. Thus, operation check (such as inspection associated with operation) can be performed under the condition of the control unit. Moreover, the micropump can be immediately brought into usable condition by slidingly inserting the tube unit.

Twentieth Aspect

A twentieth aspect of the invention is directed to a tube unit attachable to and detachable from the control unit of the above aspects, the tube unit including: a tube having elasticity and a circular-arc-shaped part; a plurality of fingers which extend in the radial directions from the center of the circular-arc shape of the tube; and a tube guide frame which holds the tube and the plural fingers.

According to this aspect of the invention, the tube is kept opened under the condition of the tube unit. Accordingly, decrease in delivery accuracy due to deterioration of restoration caused by continuous closure of the tube can be prevented.

The tube unit includes the tube and the plural fingers. The outside diameter (inside diameter) of the tube easily varies, and the flow amount of fluid per unit time changes according to the variation. Thus, desired flow amount with small variation can be secured by providing the tube and the fingers having lengths matched with the outside diameter of the tube on the tube unit.

BRIEF DESCRIPTION OF THE DRAWINGS

The invention will be described with reference to the accompanying drawings, wherein like numbers reference like elements.

FIGS. 4A to 4C are front views illustrating the disassembled micropump according to the first embodiment.

FIG. 6A is a cross-sectional view taken along a line A-P-A in FIG. 5, and FIG. 6B is a cross-sectional view taken along a line F-F in FIG. 6A.

FIG. 11A is a partial plan view, and FIG. 11B is a cross-sectional view taken along a line E-E in FIG. 11A.

FIG. 12A is a partial plan view, and FIG. 12B is a cross-sectional view taken along a line H-H in FIG. 12A.

FIG. 13A is a partial plan view, and FIG. 13B is a cross-sectional view taken along a line M-M in FIG. 13A.

DESCRIPTION OF EXEMPLARY EMBODIMENTS

Exemplary embodiments according to the invention are hereinafter described with reference to the drawings.

Figure 9:
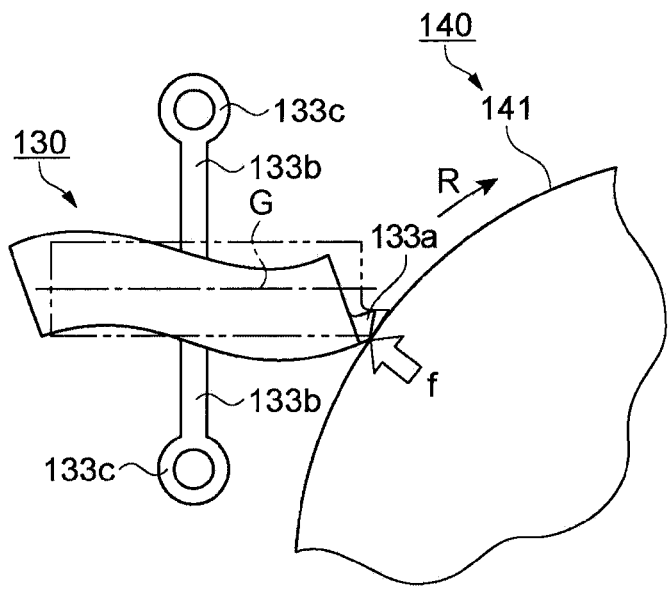
FIG. 9 is a partial plan view schematically illustrating operation of the oscillator according to the first embodiment.
Figure 10:
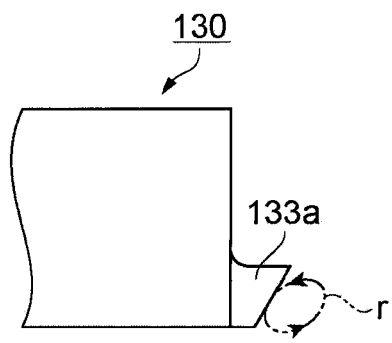
FIG. 10 schematically illustrates movement of a projection on the oscillator according to the first embodiment.
Figure 11A:
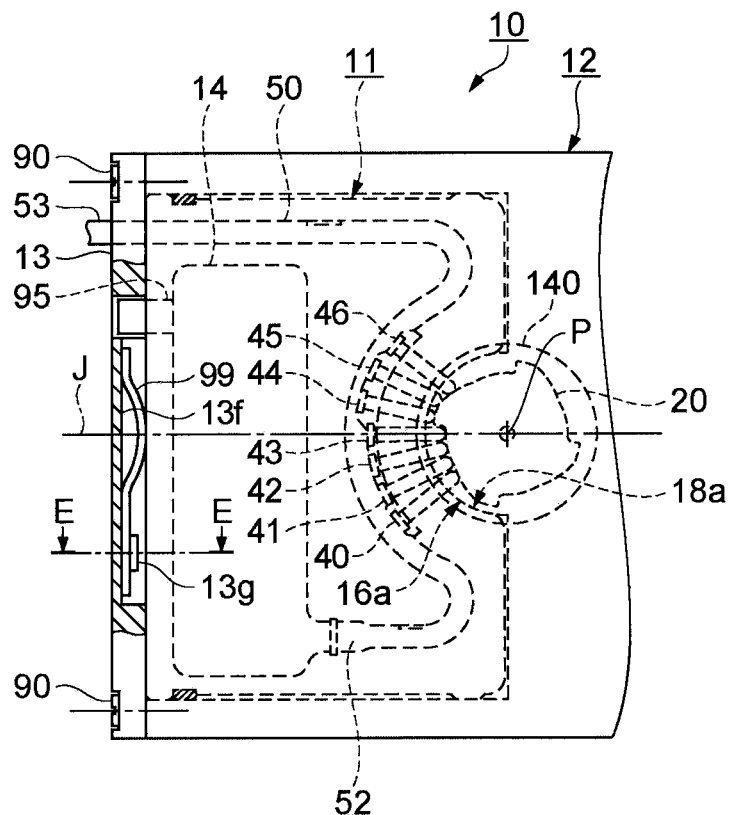
FIGS. 11A and 11B show a micropump according to a second embodiment.
Figure 11B:
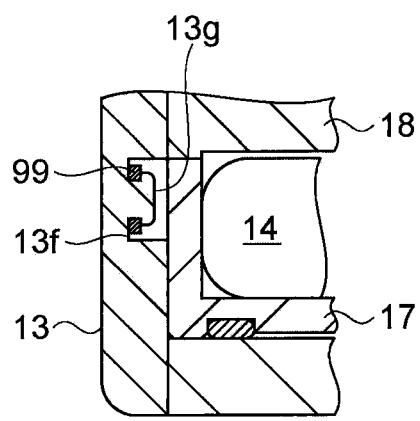
Figure 12A:
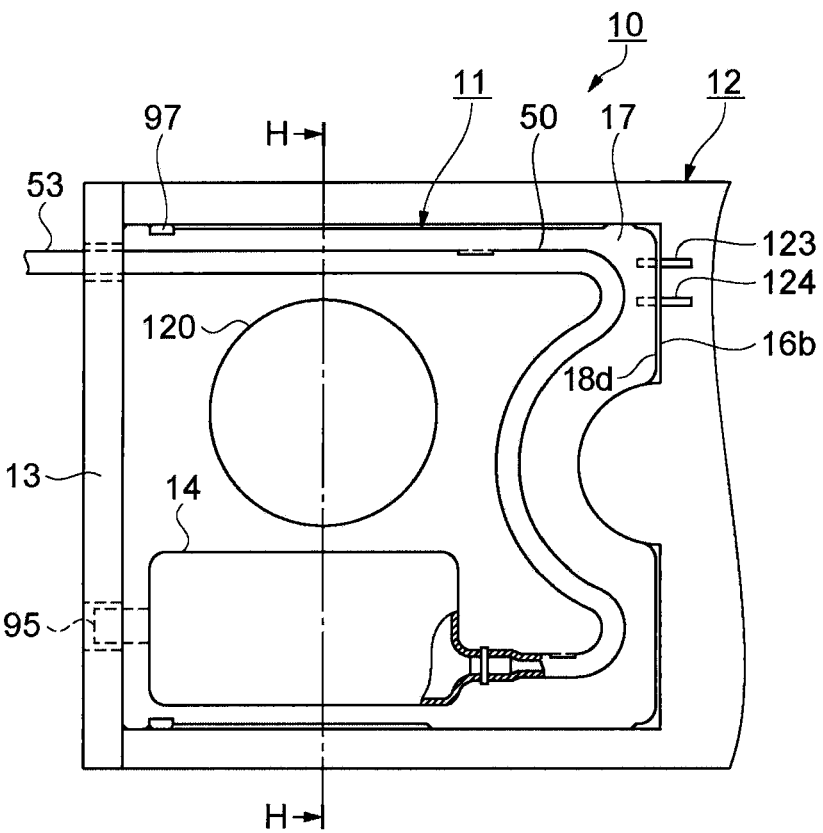
FIGS. 12A and 12B show a micropump according to a third embodiment.
Figure 12B:
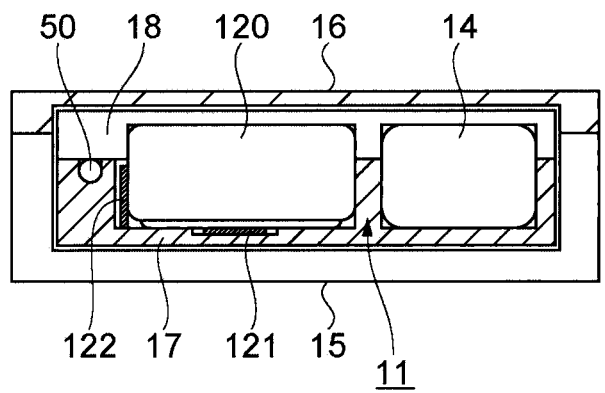
Figure 13A:
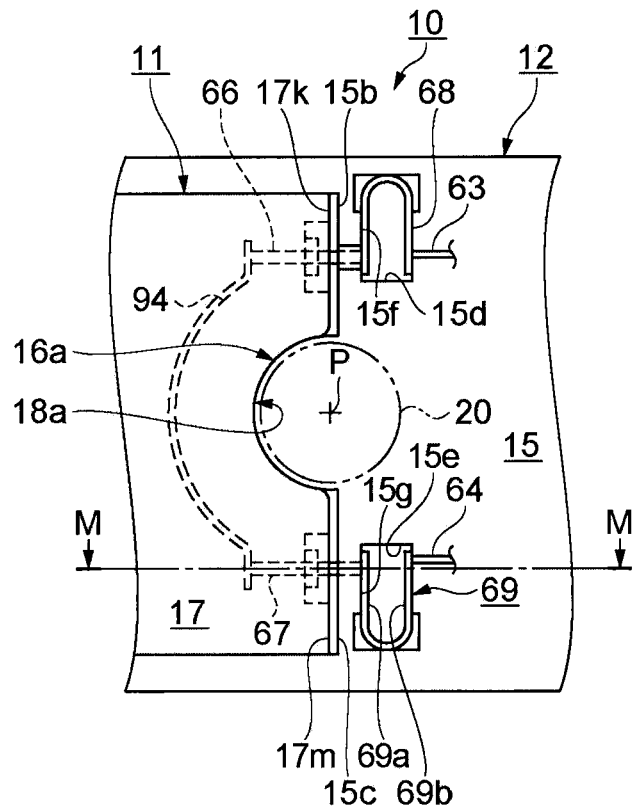
FIGS. 13A and 13B show a micropump according to a fourth embodiment.
Figure 13B:
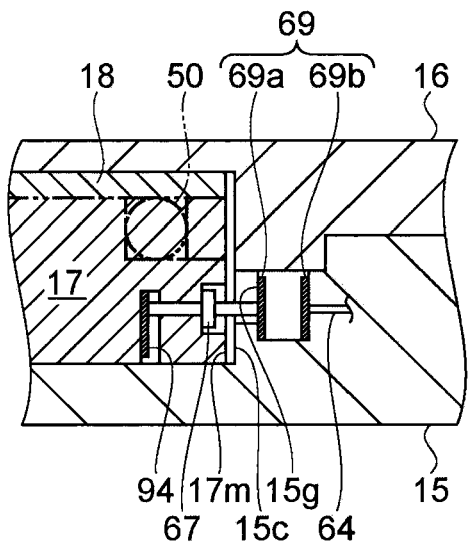
Figure 14:
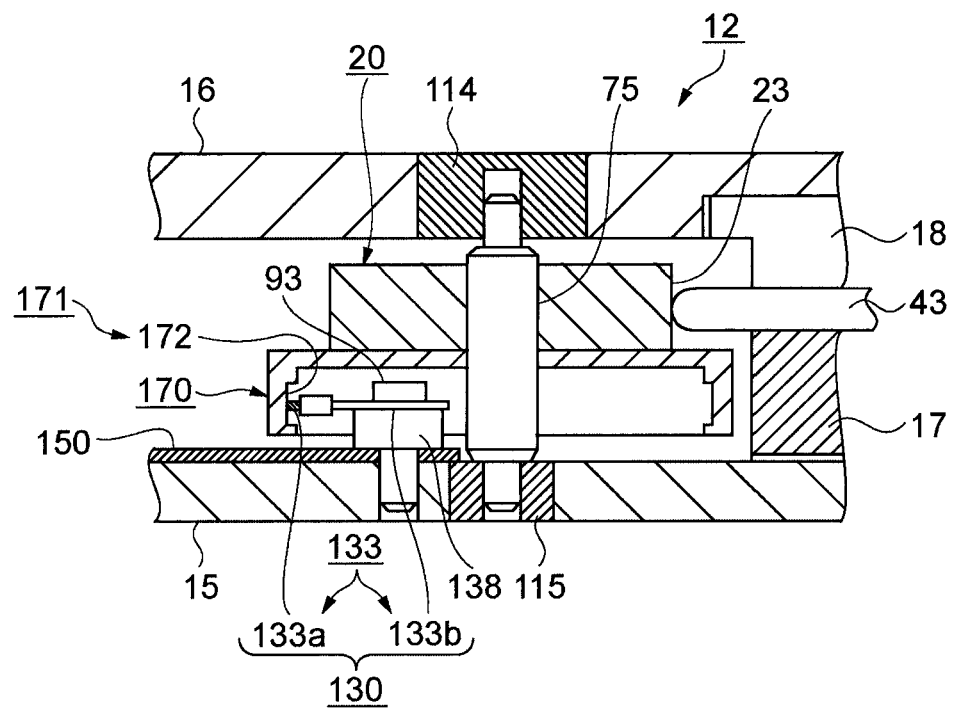
FIG. 14 is a partial cross-sectional view showing a part of a control unit according to a fifth embodiment.
Figure 15:
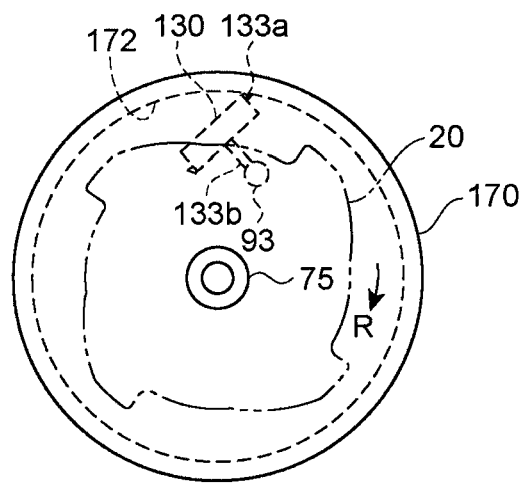
FIG. 15 is a plan view showing a rotor according to the fifth embodiment.
Figure 16:
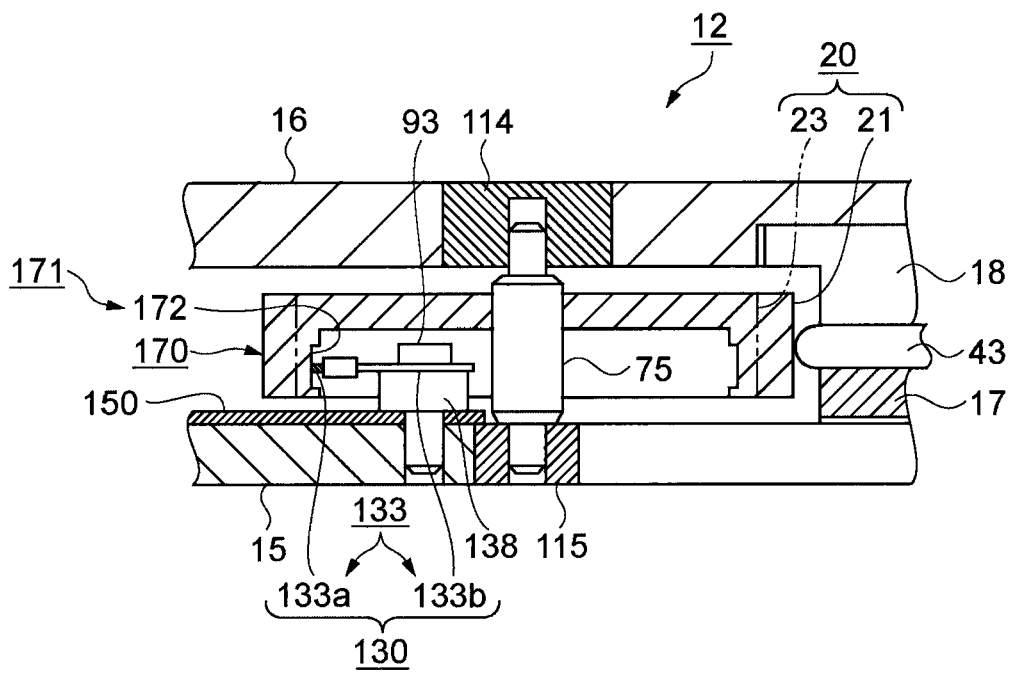
FIG. 16 is a partial cross-sectional view showing a part of a control unit according to a sixth embodiment.
Figure 17:
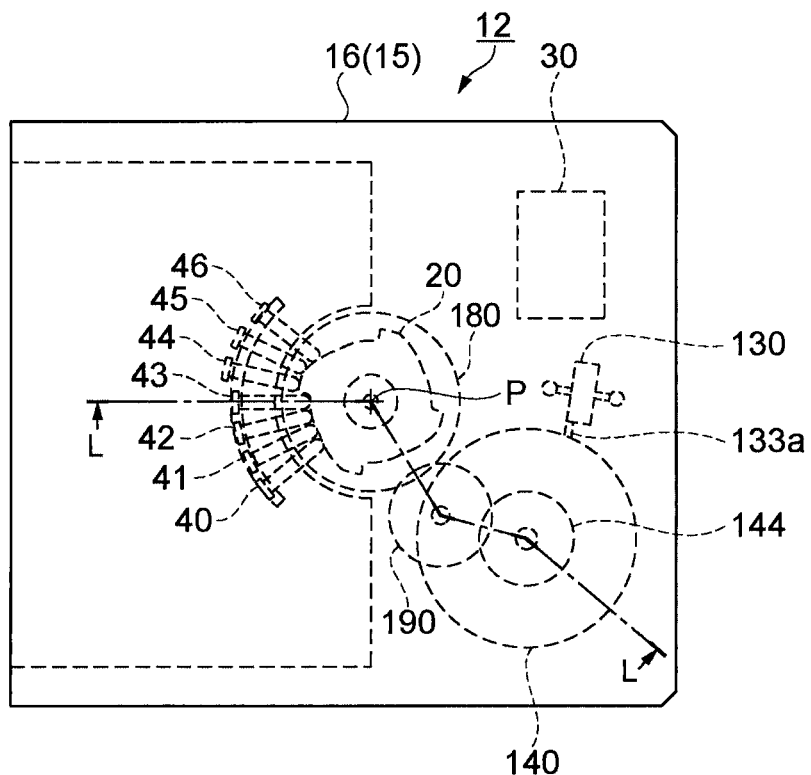
FIG. 17 is a plan view showing a control unit according to a seventh embodiment.
Figure 18:
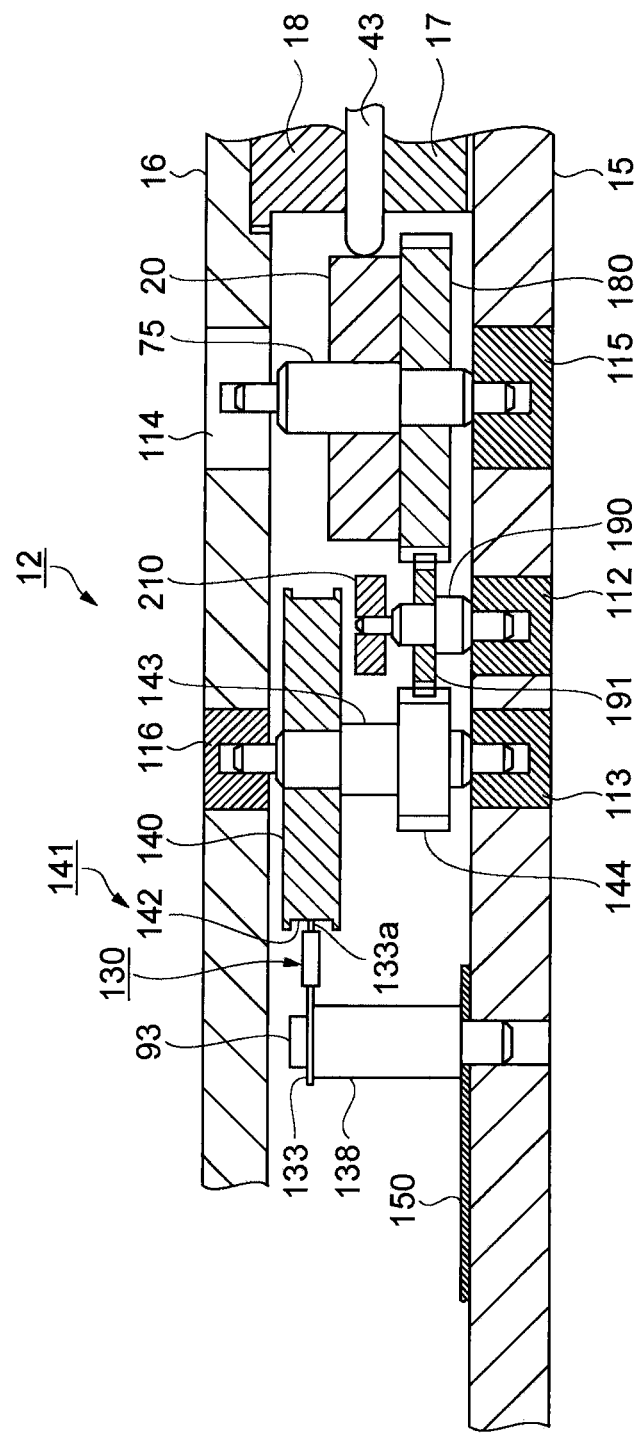
FIG. 18 is a partial cross-sectional view taken along a line L-L in FIG. 17.

FIGS. 1 through 10 illustrate a micropump according to a first embodiment, FIGS. 11A and 11B illustrate a micropump in a second embodiment, FIGS. 12A and 12B illustrate a micropump in a third embodiment, FIGS. 13A and 13B illustrate a micropump in a fourth embodiment, FIGS. 14 and 15 illustrate a micropump in a fifth embodiment, FIG. 16 illustrates a micropump in a sixth embodiment, and FIGS. 17 and 18 illustrate a micropump in a seventh embodiment.

The figures referred to in the following description are only schematic illustrations containing vertical and horizontal reduction scales different from the actual ones of the components and parts in the micropump for easy understanding of the figures.

First Embodiment

Figure 1:
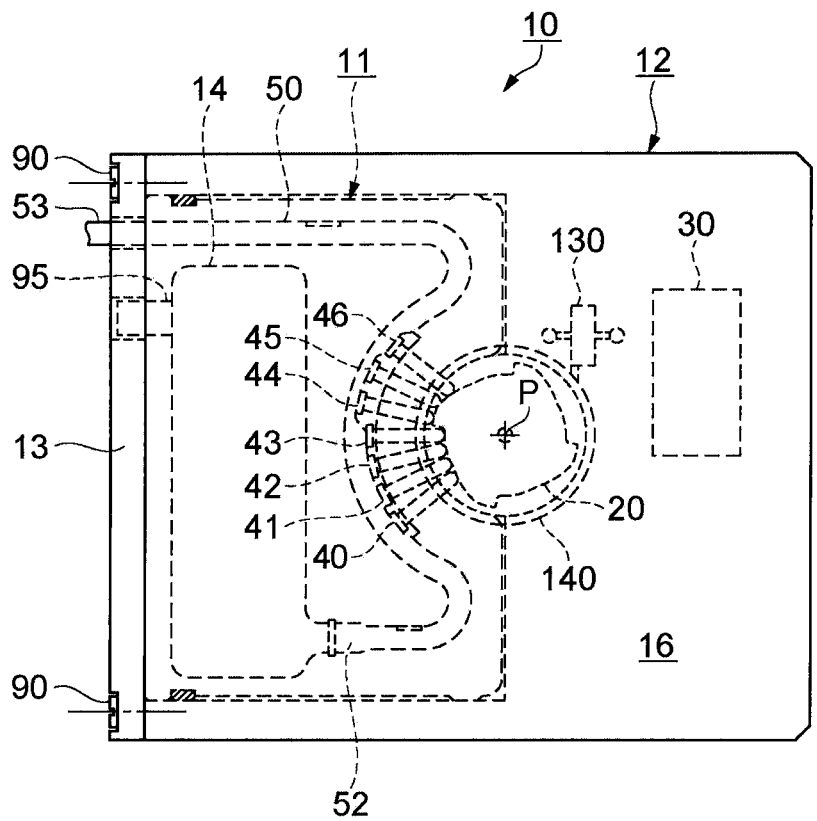
FIG. 1 is a plan view illustrating a general appearance of a micropump according to a first embodiment.
Figure 2:
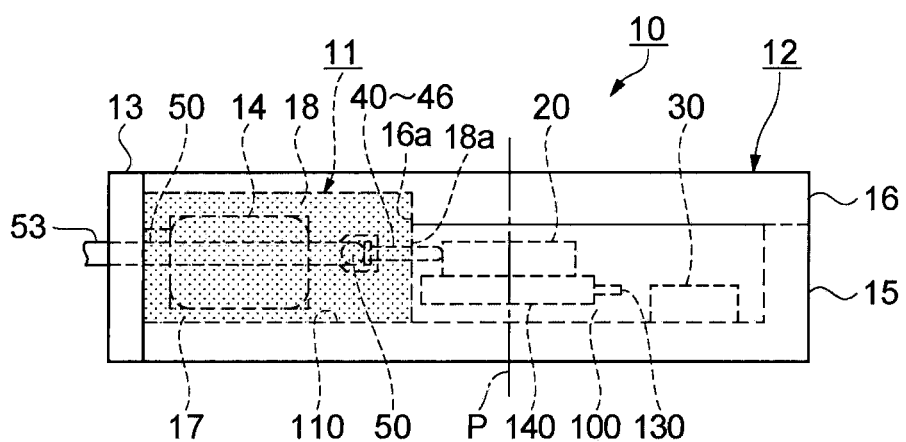
FIG. 2 is a front view illustrating a general appearance of the micropump according to the first embodiment.

FIG. 1 is a plan view illustrating a general appearance of a micropump in the first embodiment, and FIG. 2 is a front view of the general appearance of the micropump. As illustrated in FIGS. 1 and 2, a micropump 10 includes a tube unit 11 slidingly inserted into a control unit 12 through an opening provided on its left side in the figure. The tube unit 11 is fixed to the control unit 12 by a fixing frame 13 as a cover member using fixing screws 90 to be combined as one unit.

The tube unit 11 includes a tube 50 having elasticity and a circular-arc portion, a first tube guide frame 17 and a second tube guide frame 18 as tube guide frames for holding the tube 50, and a reservoir 14 communicating with a flow inlet portion 52 of the tube 50 and containing fluid. In the following description, it is assumed that fluid is liquid such as liquid medicine.

The control unit 12 includes a cam 20, a rotor 140 held coaxially with the cam 20, an oscillator 130 for providing rotational force to the rotor 140, and a control circuit unit 30 for inputting drive signals to the oscillator 130 for drive control.

The cam 20, the oscillator 130, and the control circuit unit 30 are supported within a space 100 formed by a first device frame 15 and a second device frame 16.

One end of the tube 50 corresponds to a flow outlet portion 53 which penetrates through the fixing frame 13 and projects to the outside to deliver liquid from the reservoir 14 to the outside.

A septum 95 as a port for injecting liquid into the reservoir 14 or for sealing is provided on a part of the reservoir 14. The septum 95 projects from the reservoir 14 to such an extent as not to project from the fixing frame 13.

The structures and assembly method of the tube unit 11, the control unit 12, and the fixing frame 13 are now discussed.

Figures 3A, 3B, 3C:
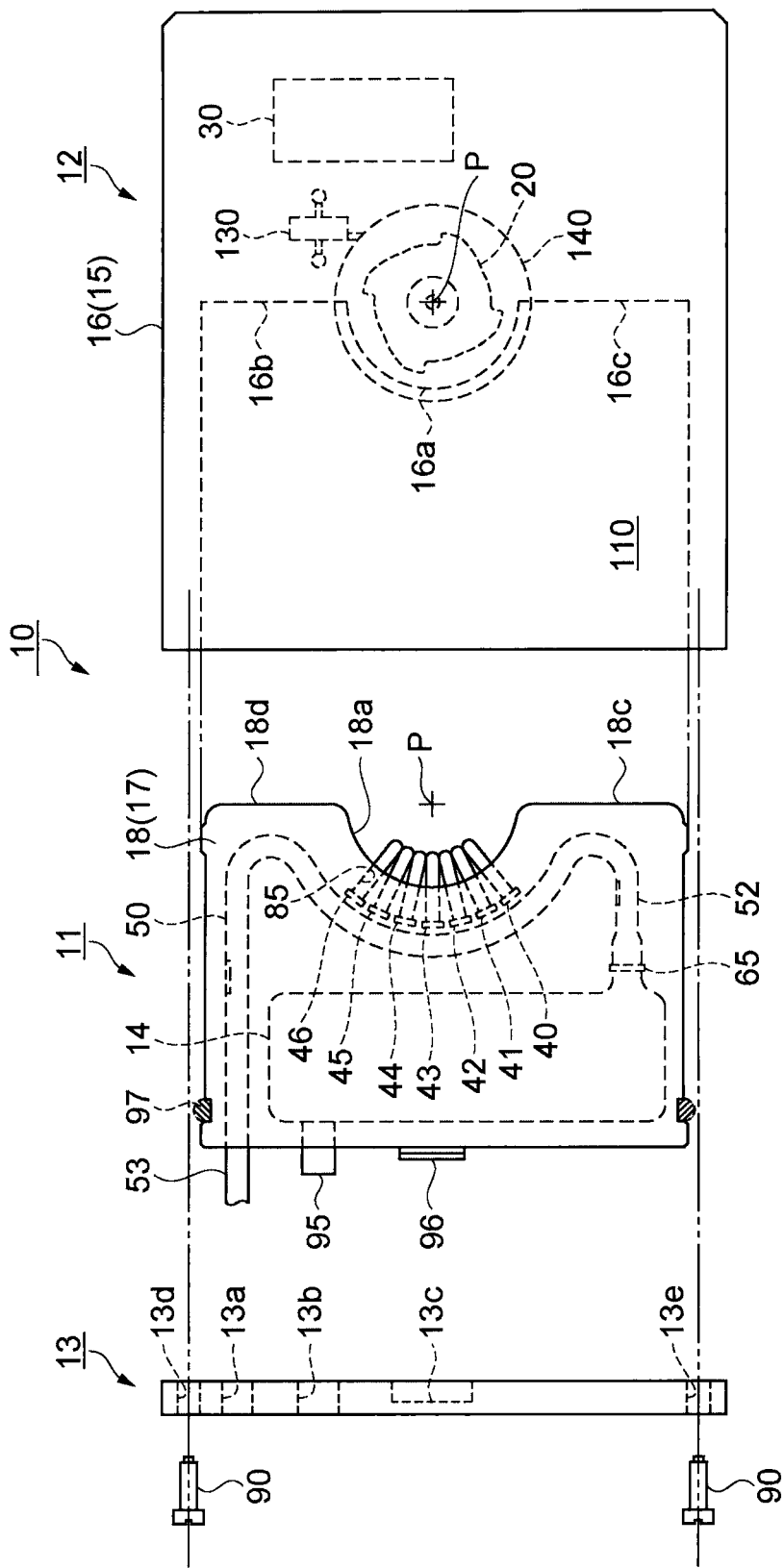
FIGS. 3A to 3C are plan views illustrating the disassembled micropump according to the first embodiment.

FIGS. 3A to 3C are plan views illustrating the disassembled micropump, and FIGS. 4A to 4C are front views illustrating the disassembled micropump. FIGS. 3A and 4A show the fixing frame 13, FIGS. 3B and 4B show the tube unit 11, and FIGS. 3C and 4C show the control unit 12.

As illustrated in FIGS. 3A to 4C, the control unit 12 has spaces 100 and 110 formed by the first device frame 15 and the second device frame 16. The space 100 contains the cam 20 (including the rotor 140), the oscillator 130, and the control circuit unit 30. The space 110 having the opening on one side is a space into which the tube unit 11 is inserted.

The tube unit 11 contains the tube 50 and the reservoir 14 communicating with each other and is held by the first tube guide frame 17 and the second tube guide frame 18. Fingers 40 through 46 attached into finger guide holes 85 formed by the first tube guide frame 17 and the second tube guide frame 18 are slidingly inserted into the space 110 of the control unit 12 from the left side in the figure.

One ends of the fingers 40 through 46 project toward the control unit 12 and contact the outer circumferential side surface of the cam 20 when the tube unit 11 is inserted into the control unit 12.

The cam 20 rotates around a rotation center P as axis. Thus, the tube unit 11 is inserted into the control unit 12 in parallel with the rotational flat plane of the cam 20.

A packing 97 engages with the outer circumferential surface of the tube unit 11 in the vicinity of the fixing frame 13 so as to close the spaces 100 and 110 when the tube unit 11 is inserted into the control unit 12.

The tube unit 11 is pushed into the control unit 12 (space 110) until a circular-arc-shaped (concaved) wall surface 18a contacts a wall surface 16a projecting from the control unit 12 in circular-arc shape. Both the wall surfaces 18a and 16a opposed to each other are formed in concentric circles each having its center on the rotation center P of the cam 20.

Figure 5:
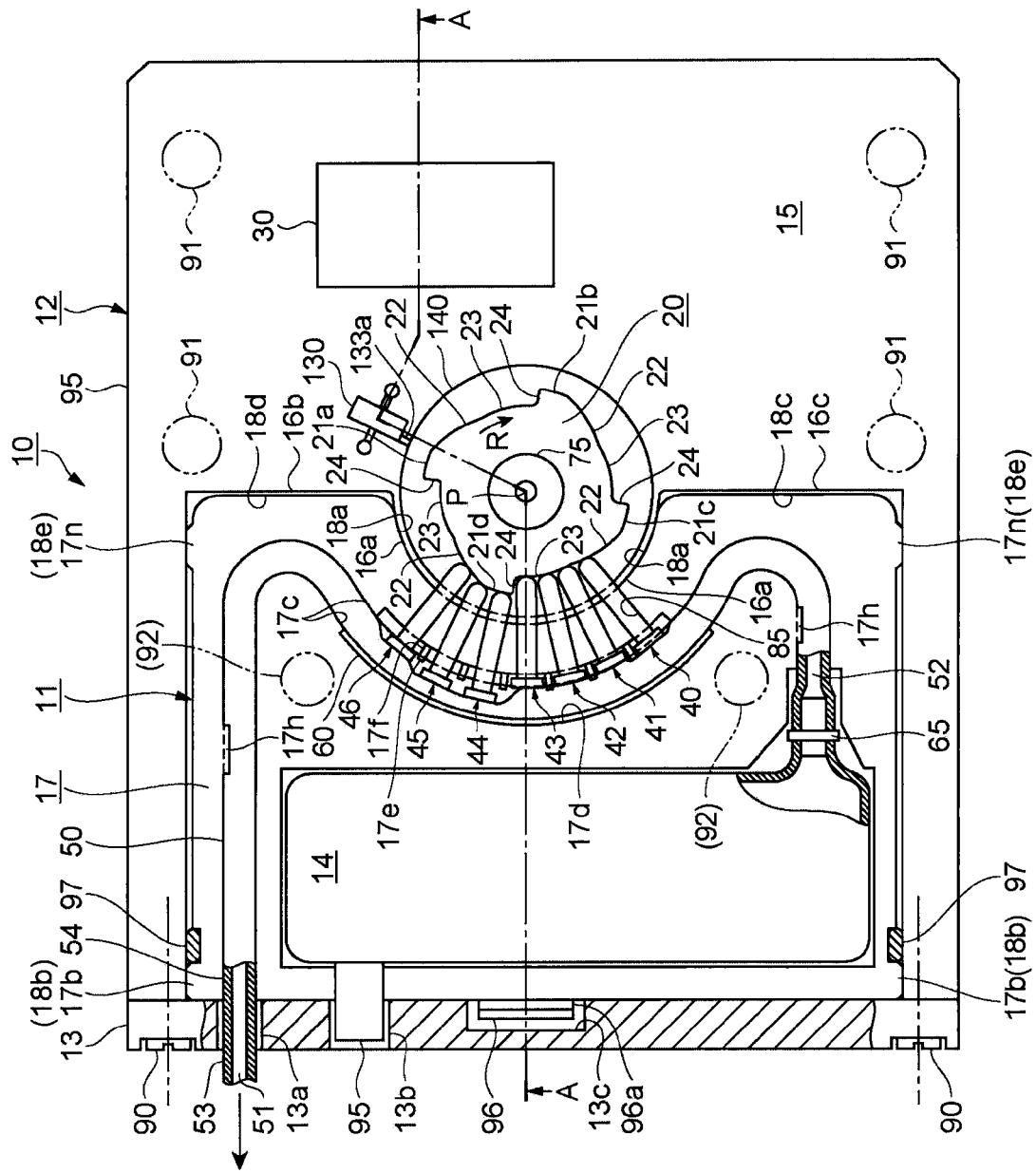
FIG. 5 is a plan view illustrating the micropump according to the first embodiment.

The control unit side ends 18c and 18d of the tube unit 11 are so sized that a clearance is produced between the inner side walls 16b and 16c of the control unit 12 when the wall surfaces 18a and 16a contact each other (see FIG. 5 as well).

This clearance is required to securely bring the wall surfaces 18a and 16a into contact with each other and to locate the circular-arc center of the circular-arc-shape portion of the tube 50 (at least the range pressed by the fingers 40 through 46) at the rotation center P of the cam 20.

After the tube unit 11 is inserted into the control unit 12, the fixing frame 13 is inserted from the back of the tube unit 11. More specifically, the fixing screws 90 are inserted into through holes 13d and 13e opened on the fixing frame 13 to fasten the fixing screws 90 to screw holes (not shown) formed on the first device frame 15 of the control unit 12.

The flow outlet portion 53 of the tube 50 and the septum 95 provided on the reservoir 14 project from the tube unit 11. The tube 50 and the septum 95 are inserted into a tube insertion hole 13a and a septum insertion hole 13b, respectively, when the fixing frame 13 is fixed. The flow outlet portion 53 extends to the outside of the fixing frame 13.

A projection 96 is formed at the end of the first tube guide frame 17. The projection 96 is used when the tube unit 11 is removed from the control unit 12. The projection 96 is contained within a concave 13c formed on the fixing frame 13.

The structures of the respective components and the operation of the micropump 10 assembled as described above are now explained with reference to the drawings.

Figure 7:
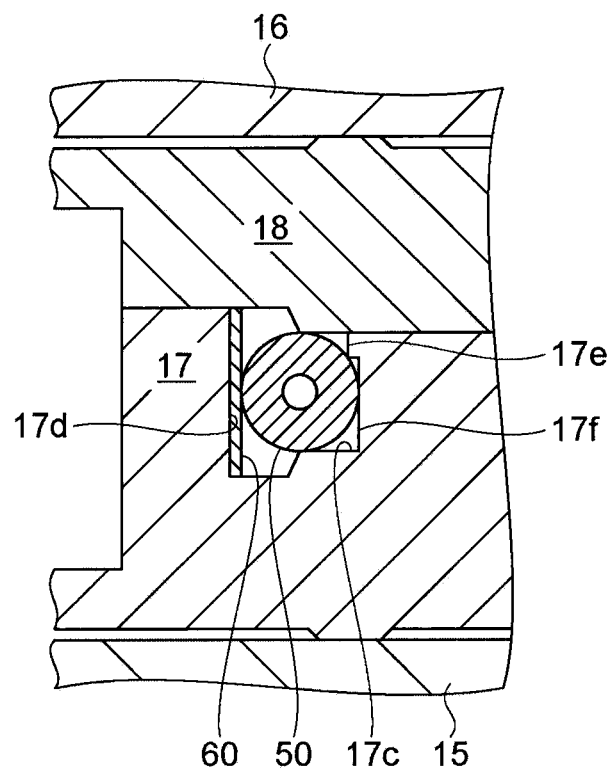
FIG. 7 is a partial cross-sectional view showing a structure for holding a tube according to the first embodiment.

FIGS. 5 through 7 illustrate the micropump and a part thereof according to this embodiment. FIG. 5 is a plan view. FIG. 6A is a cross-sectional view taken along a line A-P-A in FIG. 5. FIG. 6B is a cross-sectional view taken along a line F-F in FIG. 6A. FIG. 7 is a partial cross-sectional view showing a tube holding structure. Initially, the structure of the control unit 12 is discussed with reference to FIGS. 5, 6A and 6B.

FIG. 5 illustrates the structure as viewed through the second device frame 16 and the second tube guide frame 18.

The control unit 12 has the cam 20 constructed such that the rotation center P of the cam 20 can be located approximately at the center of the circular-arc shape of the tube 50 a part of which is disposed in circular-arc shape on the tube unit 11 in the plan view under the condition in which the tube unit 11 is attached to the control unit 12.

The control unit 12 further includes the disk-shaped rotor 140 for transmitting rotational force to the cam 20, the oscillator 130 disposed such that a projection 133a contacts the outer circumferential side surface of the rotor 140, and the control circuit unit 30.

The cam 20 and the rotor 140 are held by a cam shaft 75. Thus, the cam 20 and the rotor 140 are constructed in such a manner as to rotate as one body around the common axis of the rotation center P.

As illustrated in FIG. 5, the control circuit unit 30, the oscillator 130, and the cam 20 are dispersed at positions not overlapping with one another on a flat plane.

The cam 20 is uneven in the outer circumferential direction, and has finger pressing surfaces 21a through 21d on the outermost circumferential part. The finger pressing surfaces 21a through 21d are disposed on a concentric circle at equal distances from the rotation center P.

Each pitch in the circumferential direction and external shape of the pair of the finger pressing surface 21a and the finger pressing surface 21b, the pair of the finger pressing surface 21b and the finger pressing surface 21c, the pair of the finger pressing surface 21c and the finger pressing surface 21d, and the pair of the finger pressing surface 21d and the finger pressing surface 21a are equalized. Also, each pitch between the finger pressing surfaces is uniform.

Each of the finger pressing surfaces 21a through 21d connects with a finger pressing slope 22 and a circular-arc portion 23 on a concentric circle around the rotation center P. The circular-arc portion 23 is located at a position not pressing the fingers 40 through 46.

One end of each of the finger pressing surfaces 21a, 21b, 21c, and 21d is connected with the corresponding circular-arc portion 23 by a linear portion 24 extended from the rotation center P.

Under the condition shown in FIGS. 5 and 6, the fingers 40 through 46 can advance and retreat along the finger guide holes 85 provided in one-to-one correspondence with the fingers 40 through 46. The fingers 40 through 46 are pressed toward the tube 50 by the cam 20 to close a liquid flow portion 51 by pressing the tube 50. The center positions of the fingers 40 through 46 in the cross-sectional direction are located approximately at the center of the tube 50.

The cross-sectional structure of the control unit 12 is now discussed with reference to FIGS. 6A and 6B. The first device frame 15 and the second device frame 16 are stacked and closely fixed by using fixing screws 91 provided on the peripheries of the first and second device frames 15 and 16 (see FIG. 5).

Under the condition in which the first device frame 15 and the second device frame 16 are fixed to each other, the space 100 is produced inside the first and second frames 15 and 16. The cam 20, the rotor 140, the oscillator 130, and the control circuit unit 30 are disposed within the space 100.

The cam shaft 75 is supported by a bearing 114 provided on the second device frame 16 and a bearing 115 provided on the first device frame 15. Each insertion hole of the bearings 114 and 115 on the first device frame 15 and the second device frame 16 does not penetrate through the frames 15 and 16.

A groove 141 is formed on the outer circumferential side surface of the rotor 140 in the rotation direction. A contact surface 142 to contact the oscillator 130 is formed on the inner side surface of the groove 141.

The oscillator 130 is disposed approximately at the center in the cross-sectional direction of the groove 141 of the rotor 140. The end of a reinforcing plate 133 is fixed to a fixing shaft 138 by a fixing screw 93. The structure and operation of the oscillator 130 will be described later with reference to FIGS. 8 through 10.

A circuit board 150 is provided on the inner surface of the first device frame 15 (bottom of the space 100), and a connection pattern (not shown) is formed on the surface of the circuit board 150. The control circuit unit 30 is connected and fixed to the upper surface of the circuit board 150.

The control circuit unit 30 contains a power source circuit, oscillation circuit (both not shown) and the like. The power source circuit is connected with an electrode of a battery (not shown) as power source via the connection pattern. The oscillation circuit is connected with plural electrodes of the oscillator 130.

The structure of the tube unit 11 is now discussed with reference to FIGS. 5, 6A, 6B, and 7.

The tube unit 11 includes the tube 50 having elasticity and a circular-arc-shaped part, the first tube guide frame 17 and the second tube guide frame 18 as tube guide frames for holding the tube 50, and the reservoir 14 communicating with the flow inlet portion 52 of the tube 50 and containing liquid.

The tube 50 is attached within a tube guide groove 17c formed on the first tube guide frame 17.

The flow inlet portion 52 of the tube 50 communicates with the reservoir 14. The other end of the tube 50 is the flow outlet portion 53 passing through the tube insertion hole 13a of the fixing frame 13.

The flat shape and flat surface position of the tube 50 are regulated by attaching approximately the entire area of the tube 50 within the tube guide groove 17c. Projections as tube holding portions are formed on a part of the inner side wall of the tube guide groove 17c to prevent upward rising of the tube 50.

FIG. 7 is a partial cross-sectional view showing a part of these projections. FIG. 7 shows a projection between the finger 45 and the finger 46 in the adjoining pairs of the fingers 40 through 46 as an example (see FIG. 5 as well).

A tube guide side wall 17f is provided on the tube guide groove 17c between the finger 45 and the finger 46 as a projection portion having a width not preventing advance and retreat of the fingers 45 and 46. A projection 17e projecting toward an upper part of the tube 50 is formed on the upper region of the tube guide side wall 17f.

The tube guide side wall 17f and the projection 17e provided between each adjoining pair of the fingers 40 through 46 regulate the position of the tube in the flat plane direction and rising of the tube within the position range the fingers 40 through 46.

According to this embodiment, projections 17h similar to the projection 17e are disposed at positions of the tube 50 close to the flow outlet portion 53 and close to the flow inlet portion 52 as illustrated in FIG. 5. The projections 17h prevent rising of the tube 50 in the region other than the circular-arc-shaped portion until the second tube guide frame 18 is attached.

The fingers 40 through 46 are attached to the finger guide holes 85 penetrating at equal intervals from the rotation center P of the cam 20 in the radial directions. The fingers 40 through 46 have the same shape, and thus only the finger 43 is herein discussed as an example.

As illustrated in FIG. 6A, the finger 43 has a cylindrical shaft portion 43a, a fringe-shaped tube pressing portion 43c provided at one end of the shaft portion 43a, and a cam contacting portion 43b having the other end rounded in hemispherical shape. The fingers 40 through 46 can advance and retreat in the axial direction along the finger guide holes 85.

As illustrated in FIG. 6B, each of the finger guide holes 85 is produced by forming a substantially U-shaped groove 17a on the first tube guide frame 17, and closing the upper opening as viewed in the figure by the second tube guide frame 18.

The position of the finger 43 in the cross-sectional direction is regulated by attaching the shaft portion 43a to the groove 17a from above the opening and then attaching the second tube guide frame 18 to the first tube guide frame 17 from above.

As illustrated in FIG. 6A, the shift position in the axial direction is regulated by disposing the tube pressing portion 43c between the tube guide groove 17c and the tube 50.

Under the condition in which the tube 50, the reservoir 14, and the fingers 40 through 46 are attached to the first tube guide frame 17, the first tube guide frame 17 and the second tube guide frame 18 are brought into close contact with each other by the respective junction surfaces, and are fixed by fixing screws 92.

The tube unit 11 having this structure is slidingly inserted into the space 110 (see FIG. 4C) formed in the control unit 12.

Under the condition in which the first tube guide frame 17 and the second tube guide frame 18 are fixed to each other, the clearance between the portion of the tube 50 in the vicinity of the flow outlet port 53 and the tube unit 11 is closed by packing, adhesive or the like. By this method, the interior of the tube unit 11 becomes closed structure.

The packing 97 engages with the outer circumference of the tube unit 11 near the fixing frame 13. Under the condition in which the tube unit 11 is inserted into the control unit 12, the interior becomes closed space, thereby providing waterproof structure and dustproof structure of the micropump 10.

When waterproof of the micropump 10 is not required, the packing 97 can be eliminated.

As illustrated in FIGS. 5 through 7, a tube regulating wall 17d constituted by a concave along the tube guide groove 17c is provided at least in the range of the tube guide groove 17c for pressing the tube 50 by the fingers 40 through 46.

An elastic member 60 is provided within the concave. That is, the elastic member 60 is disposed between the tube 50 and the tube regulating wall 17d. The elastic member 60 becomes damper when the tube 50 is pressed by the fingers 40 through 46 so as to prevent deterioration of the tube 50. The elastic member 60 has biasing force necessary for closing the tube. It is preferable that the friction coefficient between the tube 50 and the elastic member 60 is small.

An air vent filter 65 is provided at a communicating portion between the tube 50 and the reservoir 14 as a communicating member. A lyophilic filter having small pores is equipped inside the air vent filter 65. This filter transmits liquid and blocks passage of bubbles.

The pores formed in the filter are in the range from 0.1 to 1 μm so sized as to transmit liquid and prevent entrance of bubbles equal to or larger than 0.1 μm, or equal to or larger than 1 μm which are produced in the reservoir 14 into the tube 50.

A part or the entire area of the first tube guide frame 17 and the second tube guide frame 18 constituting the outer periphery of the tube unit 11, and a part or the entire area of the first device frame 15 and the second device frame 16 constituting the outer periphery of the control unit 12 are transparent.

In this case, the inside components and the engagement relations and drive conditions of the components can be visually recognized, and whether the respective components are in the normal condition, where the faulty portion exists, and others can be visually checked and detected. When the reservoir 14 is transparent, the liquid quantity contained in the reservoir 14 can be visually checked. The transparent area may be provided only in the area desired to be visually checked.

As illustrated in FIGS. 5 and 6A, projections 17b are formed on the outside surface of the base side (fixing frame 13 side) of the first tube guide frame 17, and projections 17n are formed on the outside surface of the end side of the first tube guide frame 17. Also, projections 18b and 18e are formed on the outside surfaces of the base and end sides of the second tube guide frame 18, respectively.

Under the condition in which the first tube guide frame 17 and the second tube guide frame 18 are joined with each other, the projections 17b and 18b become ring-shaped continuous projections, and the projections 17n and 18e become ring-shaped continuous projections.

In slidingly inserting the tube unit 11 into the control unit 12, the projections 17b, 17n, 18b, and 18e increase accuracy in the positions of the control unit 12 and the tube unit 11 and reduce resistance produced at the time of insertion or removal.

The projection 96 having a groove 96a is formed on the back (fixing frame 13 side) of the tube unit 11. This projection 96 is used for removing the tube unit 11 from the control unit 12.

The liquid transportation performed by the micropump 10 according to this embodiment is now explained. Initially, the structure and operation of the oscillator 130 are discussed with reference to FIGS. 8 through 10.

Figure 8:
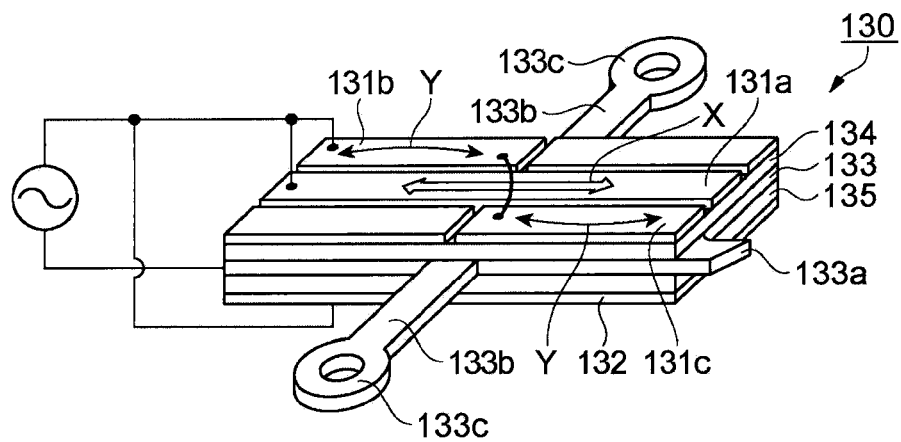
FIG. 8 is a perspective view showing a structure of an oscillator according to the first embodiment.

FIG. 8 is a perspective view showing the structure of the oscillator. As illustrated in FIG. 8, the oscillator 130 has a substantially rectangular thin-plate shape. The oscillator 130 has a laminated structure including a plate-shaped piezoelectric element 134 on the front surface of the reinforcing plate 133, and electrodes 131a, 131b, and 131c on the front surface of the piezoelectric element 134.

A plate-shaped piezoelectric element 135 is closely attached to the back surface of the reinforcing plate 133, and an electrode 132 is laminated on the front surface of the piezoelectric element 135. The electrode 131a is disposed at the center of the piezoelectric element 134 in the width direction throughout the length of the piezoelectric element 134. The electrodes 131b and 131c are disposed diagonally with the electrode 131a located between the electrodes 131b and 131c.

Though not shown in the figure, the electrode 132 and the electrodes 131a, 131b, and 131c are formed plane symmetric with respect to the reinforcing plate 133.

The materials of the piezoelectric elements 134 and 135 are not particularly limited. For example, lead zirconate titanate (PZT), crystal, lithium niobate, barium titanate, lead titanate, lead metaniobate, polyvinylidene fluoride, lead zinc niobate, and lead scandium niobate may be employed.

The reinforcing plate 133 has function as common electrode for the piezoelectric elements 134 and 135, and function for reinforcing the entire area of the oscillator 130 to prevent damage of the oscillator 130 caused by excessive amplitude, external force or the like. The material of the reinforcing plate 133 is not particularly limited. For example, stainless steel, aluminum or aluminum alloy, titanium or titanium alloy, copper or copper alloy, and other metal material may be used.

It is preferable that each thickness of the piezoelectric elements 134 and 135 is larger than that of the reinforcing plate 133. In this case, the oscillator 130 can be oscillated with higher efficiency.

The piezoelectric elements 134 and 135 repeatedly expand and contract in the longitudinal direction when alternating voltage is applied thereto. With expansion and contraction of the piezoelectric elements 134 and 135, the reinforcing plate 133 repeatedly expands and contracts in the longitudinal direction accordingly.

The projection 133a is formed integrally with the end of the reinforcing plate 133 in the longitudinal direction. As illustrated in FIGS. 5 and 6A, the projection 133a of the oscillator 130 is disposed in such a position as to contact the outer circumferential side surface (contact surface 142) of the rotor 140.

The projection 133a is disposed at a position (a corner of the structure shown in the figure) shifted from the center (center line G: see FIG. 9) of the reinforcing plate 133.

A pair of arms 133b project on both sides of the center of the reinforcing plate 133 in the longitudinal direction, and a fixing portion 133c is provided at each end of the arms 133b. The oscillator 130 is fixed to the first device frame 15 by attaching the fixing portions 133c to the fixing shaft 138 using the fixing screw 93 (see FIGS. 5 and 6A). That is, the oscillator 130 is supported by the arms 133b. By this method, the oscillator 130 can freely oscillate with relatively large amplitude.

The operation of the oscillator 130 is now discussed with reference to the drawings.

FIG. 9 is a partial plan view schematically illustrating the operation of the oscillator, and FIG. 10 schematically illustrates movement of the projection. As illustrated in FIG. 8, the piezoelectric element 134 in the area overlapping with the lower surface of the electrode 131a expands and contracts in the longitudinal direction as indicated by an arrow X to perform vertical oscillation when alternating voltage is applied between the electrodes 131a, 131b, and 131c, and the reinforcing plate 133.

Similarly, the piezoelectric element 134 in the area overlapping with the lower surfaces of the electrodes 131b and 131c expands and contracts in the longitudinal direction. However, since the electrodes 131b and 131c are disposed in the diagonal direction of the piezoelectric element 134, the piezoelectric element 134 in this area performs bending oscillation as indicated by an arrow Y.

For the piezoelectric element 135, similar alternating voltage is applied to the electrode 132 (the electrode 132 and the electrodes 131a, 131b, and 131c are plane symmetric).

Thus, the oscillator 130 chiefly performs vertical oscillation in the longitudinal direction, and resonates vertical oscillation and bending oscillation to provide elliptic oscillation of the projection 133a. This point is now explained.

As illustrated in FIG. 9, the projection 133a receives reaction force f from the rotor 140 when the oscillator 130 rotates the rotor 140. In this embodiment, the projection 133a is disposed at a position shifted from the center line G of the oscillator 130. Thus, the oscillator 130 is deformed and oscillated in such a manner as to be bended in the in-plane direction by the reaction force f as illustrated in FIG. 9. In FIG. 9, the deformation of the oscillator 130 is exaggerated.

The frequency of the bending oscillation and the frequency of the vertical oscillation resonate with each other by selecting the frequency of the applied voltage, appropriate shape and size of the oscillator 130, the position of the projection 133a and the like. In this case, the amplitude increases, and the projection 133a displaces (elliptically oscillates) substantially along an ellipse as indicated by an arrow r in FIG. 10.

By this step, the projection 133a is pressed against the rotor 140 with stronger force for one amplitude of the oscillator 130 when the projection 133a expands and moves the rotor 140 in the rotation direction. When the projection 133a contracts and returns, the frictional force between the projection 133a and the rotor 140 decreases or disappears. Thus, oscillation of the oscillator 130 can be converted by the rotation of the rotor 140 with high efficiency.

The oscillator 130 is disposed in such a condition that the projection 133a is biased to the contact surface 142 of the outer circumferential side surface of the rotor 140 by the elasticity of the arms 133b.

Thus, when alternating voltage is applied to the piezoelectric elements 134 and 135 to oscillate the oscillator 130 under the condition that the projection 133a contacts the contact surface 142 of the rotor 140, the rotor 140 receives frictional force (pressing force) from the projection 133a at the time of expansion of the oscillator 130. By repeated application of this pressing force, the rotor 140 rotates in the clockwise direction (arrow R).

The oscillator 130 is disposed in the position substantially in parallel with the rotor 140 in the cross-sectional direction, and has a thickness smaller than that of the rotor 140. It is preferable that the thickness of the oscillator 130 is smaller than the width of the groove 141 in the cross-sectional direction formed on the outer circumferential surface of the rotor 140.

The frequency to be applied to the piezoelectric elements 134 and 135 is not particularly limited. It is preferable that this frequency is approximately equal to the resonance frequency of the oscillation (vertical oscillation) of the oscillator 130. In this case, the amplitude of the oscillator 130 increases, and the rotor 140 rotates with high efficiency and high torque.

The operation associated with the liquid transportation in this embodiment is now discussed with reference to FIG. 5. The cam 20 is rotated by the oscillator 130 via the rotor 140 (direction of arrow R in the figure). Then, the finger pressing surface 21d of the cam 20 presses the finger 44.

The finger 45 contact the joining portion between the finger pressing surface 21*d* and the finger pressing slope 22 to close the tube 50. The finger 46 on the finger pressing slope 22 presses the tube 50. However, the degree of the press by the finger 46 is smaller than that by the finger 44, and thus the finger 46 does not completely close the tube 50.

The fingers 41 through 43 are located within the range of the circular-arc portion 23 of the cam 20 as the not-pressing initial position. The finger 40 contacts the finger pressing slope 22 of the cam 20, but does not close the tube at this position.

With rotation of the cam 20 in the direction of the arrow R from this position, the fingers 45 and 46 pressed by the finger pressing surface 21*d* of the cam 20 close the tube 50 in this order. The finger 44 is separated from the finger pressing surface 21*d* and opens the tube 50. Liquid flows into the liquid flow portion 51 at positions of the tube 50 released from closure by the fingers or positions not yet closed.

With further rotation of the cam 20 by the oscillator 130, the finger pressing slope 22 sequentially presses the fingers 40, 41, 42, and 43 in this order. When the finger pressing surface 21*c* comes to press the fingers 40, 41, 42, and 43, the tube 50 is closed.

By repeating this operation, liquid flows from the flow inlet port 52 toward the flow outlet port 53 to be discharged through the flow outlet port 53.

During this operation, two of the plural fingers contact the finger pressing surface of the cam 20. When the finger pressing surface shifts to the position for pressing the next finger, the finger pressing surface presses one of the fingers. By repeating the condition for pressing two fingers and the condition for pressing one finger, at least one finger can constantly close the tube 50. The plural fingers sequentially press the tube 50 from the liquid flow-in side (flow inlet portion 52 side) to the liquid flow-out side (flow outlet port 53) to transport fluid by repeated open and closure of the tube 50. This structure of the micropump is called wriggling system.

When the tube 50 is continuously closed for a long period, delivery accuracy may decrease due to deterioration of restoration of the tube 50. According to this embodiment, however, the tube unit 11 is separable from the control unit 12 which includes the cam 20 for pressing the fingers 40 through 46 to close the tube 50. Thus, the tube 50 is kept opened while only the tube unit 11 is attached. Accordingly, decrease in delivery accuracy due to deterioration of restoration caused by continuous closure of the tube 50 can be prevented, and desired delivery accuracy can be maintained.

Restoration of the tube 50 may also deteriorate by repeating closure and open of the tube 50 for a long period. In this case, replacement of the tube is necessary. According to this embodiment, the tube unit 11 including the tube 50 can be easily replaced after use for a certain period.

Generally, the length of the outside diameter (including inside diameter) of the tube 50 considerably varies. In this case, the flow amount of liquid per unit time changes according to variations of the size of the tube 50. By setting the fingers 40 through 46 having lengths controlled according to the outside diameter of the tube 50 in the tube unit 11, desired flow amount having small variation can be secured.

The micropump 10 in this embodiment has a structure which rotates the rotor 140 by using the oscillator 130 as the rotation drive source of the cam 20. Since the rotor 140 driven by the oscillator 130 has large rotation torque, the structure can be simplified requiring no speed reduction gear mechanism included in the related art.

The tube unit 11 and the control unit 12 are attached substantially in the horizontal direction with respect to the rotation flat plane of the cam 20. Thus, the thickness of the structure can be made smaller than the stacking structure in the related art.

The tube unit 11 is detachable from the control unit 12. Thus, running cost can be reduced by using the tube unit 11 which is a low cost and includes the tube directly contacting liquid medicine or the like as disposable component, and by repeatedly using the control unit 12 which is a higher cost than that of the tube unit.

When the tube unit 11 is inserted into the control unit 12 in the horizontal direction, the fingers 40 through are brought into tube pressing condition. Thus, the coupling mechanism disposed between the motor module and the pump module in the related art is not required, and simplification of the structure and assembly easiness can be improved.

The oscillator 130 oscillates to rotate the rotor 140 when alternating voltage is applied to the piezoelectric element. Thus, electromagnetic noise is not generated, and adverse effect is not given to the peripheral devices. Moreover, electromagnetic noise generated from the peripheral devices is not given to the oscillator 130. Accordingly, risks produced by electromagnetic noise can be prevented particularly in medical treatment.

By inserting the tube unit 11 into the space 110 formed in the control unit 12, the outer periphery of the control unit 12 (i.e., first device frame 15 and second device frame 16) obtains the case function. Thus, no case for accommodating the tube unit 11 and the control unit 12 is required, and simplification of the structure and further reduction of the thickness can be achieved.

According to this embodiment, the rotor 140 is rotated by contact between the projection 133*a* of the oscillator 130 and the outer circumferential surface of the rotor 140 (contact surface 142). In this structure, the oscillation of the oscillator 130 can be converted into rotation with high efficiency, and the rotation torque of the rotor 140 obtained when the oscillator 130 is oscillated under the same condition increases by bringing the oscillator 130 into contact with the rotor 140 having larger diameter. Thus, stable operation can be continued.

The control circuit unit 30 and the oscillator 130 do not overlap with the cam 20 in a flat plane. Thus, the thickness of the control unit 12 can be reduced, contributing to further decrease in the thickness of the micropump 10.

The first tube guide frame 17 has the tube guide groove 17*c* into which the tube 50 is inserted, the tube guide side wall 17*f* for holding the tube 50 within the tube guide groove 17*c*, and the projection 17*e*. Thus, the position of the tube 50 needs to be accurately regulated to determine the range of the tube 50 pressed by the fingers 40 through 46.

The position in the major part of the tube 50 in the thickness direction of the tube 50 can be accurately regulated by regulating the position in the flat plane direction using the tube guide groove 17*c* and holding the range for pressing the tube by the fingers using the projection 17*e*.

According to the micropump 10 in this embodiment, the fingers 40 through 46 are pressed by the rotation of the cam 20 to close the tube 50. Thus, the circular-arc center of the circular-arc shape of the tube 50 and the rotation center of the cam need to agree with each other.

The center of the circular-arc shape of the tube 50 and the rotation center P of the cam 20 can be disposed at the same position at the time of attachment of the tube unit 11 to the control unit 12 by providing the guide unit constituted by the wall surface 18*a* on the tube unit 11 and the guide unit constituted by the wall surface 16*a* on the control unit 12. Thus, all of the fingers 40 through 46 can securely close the tube without using a dedicated position regulating member.

The tube regulating wall 17*d* for regulating shift of the tube 50 by the press of the fingers 40 through 46 is provided on the first tube guide frame 17, and the elastic member 60 is provided between the tube 50 and the tube regulating wall 17*d*. In this structure, excessive pressing force is absorbed by the elastic member 60 when the tube 50 is pressed by the fingers 40 through 46. By this method, the durability of the tube 50 becomes higher than that of the structure directly pressing the tube 50 against the tube regulating wall 17*d*.

A part of or the entire area of the first tube guide frame 17, the second tube guide frame 18, the first device frame 15, and the second device frame 16 constituting the outer peripheries of the tube unit 11 and the control unit 12 are transparent. In this case, the inside components and the engagement relation and the drive condition of the components can be visually recognized. Thus, whether the inside components and the drive condition are in the normal condition, where the faulty part exists, and other can be detected. When the reservoir 14 is transparent, the liquid amount within the reservoir 14 can be visually checked.

The reservoir 14 contains the septum 95 as a port for introducing liquid into the reservoir 14 or sealing the reservoir 14. Thus, additional liquid can be easily injected into the reservoir 14 under the condition in which the reservoir 14 is connected with the tube 50, or under the condition of the micropump 10.

The air vent filter 65 for blocking passage of bubbles is provided on the communicating portion between the reservoir 14 and the tube 50.

Air dissolved in liquid contained in the reservoir 14 gathers to become bubbles with elapse of time in some cases. When fluid is medicine to be injected into a living body, liquid containing bubbles may cause serious effect which cannot be overlooked.

When the air bent filter 65 for blocking passage of bubbles is provided, entrance of bubbles into the living body is prevented. Thus, safety level increases.

Second Embodiment

A second embodiment is hereinafter described with reference to the drawings. The second embodiment includes an elastic member for biasing the tube unit to the control unit. The point different from the first embodiment is chiefly explained.

FIGS. 11A and 11B show a micropump according to the second embodiment. FIG. 11A is a partial plan view, and FIG. 11B is a cross-sectional view taken along a line E-E in FIG. 11A. As illustrated in FIG. 11A, a plate spring 99 as elastic member is provided between the tube unit 11 and the fixing frame 13.

The plate spring 99 is fixed to a concaved plate spring fixing portion 13*f* formed on the fixing frame 13 on the tube unit 11 side. The force point of the plate spring 99 is located on a center line J, and the tube unit 11 is biased toward the rotation center P of the cam 20.

By this method, the wall surface 18*a* of the tube unit 11 and the wall surface 16*a* of the control unit 12 contact each other on the center line J.

As illustrated in FIG. 11B, a guide shaft 13*g* projecting from the plate spring fixing portion 13*f* of the fixing frame 13 is fixed by fixing unit such as thermal disposition for fixing the plate spring 99. The plate spring 99 is only required to be attached to the fixing frame 13 fixed to the structure without separation from the fixing frame 13 and without loss of elasticity of the plate spring 99. Thus, fixing of the plate spring 99 is not necessarily needed.

When the tube unit 11 is fixed to the control unit 12 by the fixing frame 13, a clearance in the horizontal direction (flat plane direction) may be produced between the tube unit 11 and the control unit 12 due to variances in sizes of the components of the tube unit 11, the control unit 12, and the fixing frame 13. In this case, there is a possibility that the tube 50 cannot be closed by the fingers 40 through 46.

Thus, the wall surfaces 16*a* and 18*a* are brought into contact with each other by biasing the tube unit 11 toward the control unit 12 using the plate spring 99 such that the center of the circular-arc shape of the tube 50 and the rotation center P of the cam 20 can be located substantially at the same position. By this method, the fingers 40 through 46 can securely close the tube 50.

The elastic force of the plate spring 99 is set larger than the tube pressing force of the fingers 40 through 46.

By this method, the tube unit 11 (i.e., tube 50) does not shift in the direction away from the fingers 40 through 46 at the time of closure of the tube 50 by the fingers 40 through 46. Thus, the tube can be securely closed.

According to this embodiment, the plate spring 99 is shown as an example of the elastic member. However, the elastic member is not limited to the plate spring but may be a coil spring or a flat plate having elasticity in the thickness direction. A plurality of these elastic members may be used.

Third Embodiment

A micropump according to a third embodiment is hereinafter described with reference to the drawings. In the third embodiment, the power source is accommodated in the tube unit. The point different from the first embodiment is chiefly explained.

FIGS. 12A and 12B illustrate a micropump according to the third embodiment. FIG. 12A is a partial plan view, and FIG. 12B is a cross-sectional view taken along a line H-H in FIG. 12A. As illustrated in FIGS. 12A and 12B, a compact button type battery 120 (hereinafter abbreviated as battery 120) as power source is accommodated in the tube unit 11.

The battery 120 and the reservoir 14 are both attached to the inside of a concave formed on the first tube guide frame 17, and the upper part is sealed by the second tube guide frame 18. Assuming that the lower surface of the battery 120 in the figure is the negative pole, the lower surface is connected with a negative terminal 121. Also, assuming that the upper and side surfaces are the positive pole, the side surface is connected with a positive terminal 122.

The negative terminal 121 and the positive terminal 122 are connected with connection terminals 123 and 124 embedded at the end of the first tube guide frame 17 by not-shown leads.

The connection terminals 123 and 124 project from a control unit side end 18*d* of the first tube guide frame 17 toward an inner side wall 16*d* of the control unit 12, and extends to the inside of the control unit 12. Connection terminals (not shown) electrically and independently connected with the connection terminals 123 and 124 are provided on the control unit 12, and further connected with the control circuit unit 30 (see FIG. 5).

Under the condition in which the tube unit 11 is attached to the control unit 12, power is supplied from the battery 120 to the control circuit unit 30 such that the micropump 10 can come into operable condition.

The battery 120 may be accommodated in the tube unit 11, and the reservoir 14 may be disposed outside the tube unit 11.

For changing liquid medicine to be used or replacing the tube 50 after long-term use, the possibility of insufficiency of battery capacity during use can be eliminated by replacing both the tube 50 and the battery 120 as the tube unit 11.

The battery 120 is detachable from the tube unit 11. According to the structure shown in FIGS. 12A and 12B, the battery 120 is attached and detached by removing the fixing screws 92 (see FIG. 5) for joining the first tube guide frame 17 and the second tube guide frame 18.

In this case, such a structure including a battery cover on the second tube guide frame 18 may be employed as the structure for attaching and removing the battery 120. Alternatively, the battery 120 may be attached and detached by removing the fixing frame 13 such that the battery 120 can be slidingly inserted through the back (fixing frame 13 side) of the tube unit 11.

According to this embodiment, the compact button type battery is used as battery. However, secondary batteries such as sheet battery and lithium ion battery may be employed. The sheet battery can be stacked on the reservoir 14, which contributes to increase in the capacity of the reservoir.

The secondary battery can be charged from the outside, and therefore can be repeatedly used.

Fourth Embodiment

A micropump according to a fourth embodiment is hereinafter described with reference to the drawings. In the fourth embodiment, a detection unit having connection terminal and detection terminal for detecting whether the tube unit is attached to an accurate position on the control unit is provided between the tube unit and the control unit. The point different from the first embodiment is chiefly explained.

FIGS. 13A and 13B illustrate a micropump according to the fourth embodiment. FIG. 13A is a partial plan view, and FIG. 13B is a cross-sectional view taken along a line M-M in FIG. 13A. As illustrated in FIGS. 13A and 13B, a first connection terminal 66 and a second connection terminal 67 are embedded at peninsula-shaped end portions on both sides of the circular-arc-shaped wall surface 18a of the tube unit 11.

One ends of the first connection terminal 66 and the second connection terminal 67 are electrically connected with each other by a connection lead 94. The other ends project from ends 17k and 17m of the tube unit 11 to reach the inside of the control unit 12.

The control unit 12 (first device frame 15) has substantially U-spring-shaped first detection terminal 68 and second detection terminal 69. Since the first detection terminal 68 and the second detection terminal 69 have the same shape, only the second detection terminal is now discussed as an example.

The second detection terminal 69 is bended within a concave formed on the first device frame 15 to be attached to the concave. Arms 69a and 69b of the second detection terminal 69 press the opposed side walls inside the concave.

Thus, the position of the arm 69a is regulated by a side wall 15g inside the concave. The position of the side wall 15g is accurately regulated with respect to the rotation center P of the cam 20. The end positions of the first connection terminal 66 and the second connection terminal 67 are also accurately regulated with respect to the rotation center P of the cam 20.

When the tube unit 11 is inserted into the control unit 12 until the circular-arc-shaped wall surface 18a of the tube unit 11 and the circular-arc-shaped wall surface 16a of the control unit 12 contact each other, the second connection terminal 67 electrically connects with the second detection terminal 69. Simultaneously, the first connection terminal 66 electrically connects with the first detection terminal 68.

A lead 64 is connected with the second detection terminal 69, and further connected with a detection terminal A (not shown) of the control circuit unit 30. On the other hand, a lead 63 is connected with the first detection terminal 68, and further connected with a detection terminal B (not shown) of the control circuit unit 30.

When the detection terminal A and the detection terminal B detect both electric connection between the second connection terminal 67 and the second detection terminal 69, and electric connection between the first connection terminal 66 and the first detection terminal 68, it is determined that the circular-arc-shaped wall surface 18a of the tube unit 11 and the circular-arc-shaped wall surface 16a of the control unit 12 contact each other.

Under this condition, it is determined that the center of the circular-arc shape of the tube 50 and the rotation center P of the cam 20 agree with each other, and the oscillator 130 (see FIG. 5) is brought into operable condition by the control circuit unit 30.

When both electric connection between the second connection terminal 67 and the second detection terminal 69, and electric connection between the first connection terminal 66 and the first detection terminal 68 are not produced, it is determined that operable condition is not achieved. In this case, attachment of the tube unit 11 to the control unit 12 is again carried out.

According to this embodiment, the detection unit uses contact point system. However, light detection or magnetic detection structure may be employed.

According to this structure, the prescribed closure and open of the tube 50 can be performed according to setting by operating the oscillator 130 when agreement between the center of the circular-arc shape of the tube 50 and the rotation center P of the cam 20 is detected. Thus, desired flow amount of liquid per unit time can be transported.

Fifth Embodiment

A micropump according to a fifth embodiment is hereinafter described with reference to the drawings. In the fifth embodiment, the rotor is ring-shaped, and the projection of the oscillator is disposed in such a condition as to contact the ring-shaped inner circumferential side surface of the rotor. The point different from the first embodiment is chiefly explained.

FIG. 14 is a partial cross-sectional view illustrating a part of a control unit according to the fifth embodiment, and FIG. 15 is a plan view showing a rotor. As illustrated in FIGS. 14 and 15, a rotor 170 has a circular concave on the lower surface as viewed in the figure, thereby producing a ring shape. The oscillator 130 is disposed within this concave.

A groove 171 is formed on the ring-shaped inner circumferential side surface in the rotation direction of the rotor 170. A contact surface 172 which contacts the projection 133a formed on the oscillator 130 is provided on the inner circumferential side surface of the groove 171.

The rotor 170 and the cam 20 are stacked and held by the cam shaft 75 similarly to the first embodiment such that the rotor 170 and the cam 20 can rotate as one unit.

The oscillator 130 is fixed to the fixing shaft 138 embedded in the first device frame 15 and positioned at the end of the arm 133b (see FIG. 8) by the fixing screw 93. In this case, it is preferable that the arm 133b is constituted by one arm extending in the rotation axis direction of the rotor 170 in the layout design.

The structure and operation of the oscillator 130 are similar to those in the first embodiment (see FIGS. 8 through 10).

However, the projection 133a contacts the contact surface 172 on the ring-shaped inner circumferential side surface of the rotor 170 to rotate the rotor 170 clockwise (direction of arrow R in the figure).

According to this embodiment, the rotor 170 is ring-shaped, and the projection 133a of the oscillator 130 is disposed in such a position as to contact the contact surface 172 on the ring-shaped inner circumferential side surface of the rotor 170. In this case, the oscillator 130 is located inside from the outside diameter of the rotor 170. Thus, the size can be further reduced, and the layout design of the control circuit unit 30 (see FIG. 5 as well) can be facilitated.

Sixth Embodiment

A micropump according to a sixth embodiment is hereinafter described with reference to the drawings. The structure in the sixth embodiment corresponds to the simplified structure of the fifth embodiment. In the sixth embodiment, the rotor is provided inside a circular concave formed on one flat surface of the cam, and the projection formed on the oscillator contacts the inner circumferential side surface of the concave. The point different from the fifth embodiment is chiefly explained.

FIG. 16 is a partial cross-sectional view illustrating a part of the control unit according to the sixth embodiment. As illustrated in FIG. 16, a concave is formed on the lower surface (surface on the first device frame 15 side) of the cam 20, and the oscillator 130 is disposed within this concave. Thus, the concave formed on the cam 20 corresponds to the rotor 170.

The groove 171 is formed on the inner circumferential side surface of the rotor 170, and the contact surface 172 which contacts the projection 133a formed on the oscillator 130 is provided on the inner side surface of the groove 171. Thus, the rotor function and the cam 20 are formed as one unit.

The oscillator 130 is fixed to the fixing shaft 138 embedded in the first device frame 15 and provided at the end of the arm 133b (see FIG. 8) by the fixing screw 93.

The structure and the operation of the oscillator 130 are similar to those of the first embodiment (see FIGS. 8 through 10). However, similarly to the fifth embodiment (see FIGS. 14 and 15), the projection 133a contacts the contact surface 172 on the ring-shaped inner circumferential side surface of the rotor 170 to rotate the rotor 170 clockwise.

According to this structure, therefore, the rotor 170 is provided inside the cam 20 such that the rotor 170 and the cam 20 become one body. In this case, the structure becomes more simplified, and the size can be further reduced.

Seventh Embodiment

A micropump according to a seventh embodiment is hereinafter described with reference to the drawings. In the seventh embodiment, a speed reduction mechanism or a speed increase mechanism is provided as a driving force transmission mechanism between the rotor and the cam. In this embodiment, an example of the speed reduction mechanism is discussed.

FIG. 17 is a plan view showing a control unit according to the seventh embodiment, and FIG. 18 is a partial cross-sectional view taken along a line L-L in FIG. 17. As illustrated in FIGS. 17 and 18, the speed reduction mechanism in this embodiment includes a cam gear 180 provided on the cam 20, a rotor gear 144 provided on the rotor 140, and an intermediate wheel 190 engaging with the cam gear 180 and the rotor gear 144.

The cam gear 180 and the cam 20 are held by the cam shaft 75, and supported by bearings 114 and 115. The intermediate wheel 190 has an intermediate gear 191, and supported by a bearing 112 provided on the first device frame 15 and an intermediate bearing 210. The intermediate bearing 210 is fixed to the first device frame 15 by fixing screw or the like.

The rotor gear 144 is disposed on a rotor shaft 143 for holding the rotor 140, and supported by a bearing 113 provided on the first device frame 15 and a bearing 116 provided on the second device frame 16.

The shaft holes formed on the bearings 112 through 116 do not penetrate therethrough. Thus, the space formed by the first device frame 15 and the second device frame 16 is closed when the tube unit 11 is inserted into the control unit 12.

The oscillator 130 is fixed to the fixing shaft 138 embedded in the first device frame 15 and formed at the end of the arm 133b (see FIG. 8) by the fixing screw 93.

The shape of the rotor 140 is similar to that of the first embodiment (see FIG. 6A) as an example. The groove 141 is formed on the outer circumference of the rotor 140 in the rotation direction, and the contact surface 142 contacting the projection 133a corresponds to the inner side surface of the groove 141.

The structure and operation of the oscillator 130 are similar to those of the first embodiment (see FIGS. 8 through 10), and the relationship between the oscillator 130 and the rotor 140 is also similar to that of the first embodiment. Thus, the explanation of those is not repeated.

The rotor 140 is rotated by oscillation of the oscillator 130, and the rotation of the rotor 140 is transmitted to the cam 20 via the rotor gear 144, the intermediate gear 191, and the cam gear 180. By providing the intermediate wheel 190, the cam 20 rotates in the same direction as in the first embodiment (see FIG. 5).

The tooth number ratio of the rotor gear 144 to the cam gear 180 corresponds to the speed reduction ratio, and thus the speed reduction ratio can be changed according to the tooth number ratio of the rotor gear 144 to the cam gear 180. When the intermediate wheel 190 is constituted by a large gear and a small gear, the speed reduction ratio can be further increased. In case of speed increase, the tooth number ratio of the respective gears is determined appropriate for speed increase gear mechanism.

By providing the speed reduction mechanism or speed increase mechanism between the cam 20 and the rotor 140, the rotation speed of the cam 20 can be varied while keeping the rotation speed of the rotor 140 constant. Thus, the flow amount of liquid can be appropriately controlled.

When all of the movable mechanisms such as the oscillator 130, the rotor 140, the speed reduction mechanism, and the cam 20 are disposed on the control unit 12, no connecting mechanism is required between the control unit 12 and the tube unit 11. Thus, assembly easiness increases.

According to this embodiment, the projection 133a of the oscillator 130 contacts the contact surface 142 on the outer circumferential side surface of the rotor 140. However, this embodiment can be applied to the structure of the fifth or sixth embodiment (see FIGS. 14 through 16) in which the projection 133a contacts the contact surface 172 on the inner circumferential side surface of the rotor 170.

The micropump 10 having reduced size and thickness according to the first through seventh embodiments can continuously transport stable small flow amount of liquid. Thus, the micropump 10 can be attached to the inside or the surface of a living body for development of new medicine or medical treatment such as drug delivery. The micropump 10 can be mounted inside or outside various types of devices for transportation of fluid such as water, salt water, liquid medicine, oil, aromatic liquid, ink, and gas. The micropump 10 may be used independently for flow and supply of fluid.

The entire disclosure of Japanese Patent Application No. 2008-310593, filed Dec. 5, 2008 is expressly incorporated by reference herein.

What is claimed is:

1. A micropump comprising:
    a tube unit which includes a tube having elasticity and a circular-arc-shaped part, a plurality of fingers extending in radial directions from a circular-arc center of the circular-arc-shaped part of the tube, and a tube guide frame which holds the tube and the plurality of fingers;
    a control unit including a cam for sequentially pressing the plurality of fingers from a fluid flow-in side to a fluid flow-out side of the tube, a rotor for giving rotational force to the cam, and an oscillator having a piezoelectric element that is actuated by a plurality of electrodes formed on a surface thereof, and the oscillator having a projection disposed at an end in a longitudinal direction to contact the rotor;
    a reservoir which communicates with a flow inlet portion of the tube;
    a control circuit unit which inputs a drive signal to the piezoelectric element; and
    a power source which supplies power to the control circuit unit,
    wherein
        the tube unit is attachable to and detachable from the control unit in a direction that is parallel with respect to a rotation flat plane of the cam, and the control unit completely encases the tube unit when the tube unit is inserted in the control unit,
        the plurality of electrodes include a first electrode, a second electrode, and a third electrode disposed between the first and second electrodes, the first and second electrodes being diagonally opposed to each other, and
        the oscillator is oscillated by applying alternating voltage to the piezoelectric element, rotational force is repeatedly given to the rotor from the projection, the plurality of fingers are sequentially pressed by the cam from the flow-in side to the flow-out side of the tube, and fluid is transported by repeating opening and closing of the tube.

2. The micropump according to claim 1, wherein the tube unit is inserted into a space formed in the control unit.

3. The micropump according to claim 1, wherein:
    the rotor is disk-shaped; and
    the projection is disposed in such a position as to contact an outer circumferential side surface of the rotor.

4. The micropump according to claim 1, wherein:
    the rotor is ring-shaped; and
    the projection is disposed in such a position as to contact a ring-shaped inner circumferential side surface of the rotor.

5. The micropump according to claim 1, wherein:
    the rotor is provided inside a ring-shaped concave formed on one flat surface of the cam; and
    the projection is disposed in such a position as to contact an inner circumferential side surface of the concave.

6. The micropump according to claim 1, wherein the control circuit unit, the oscillator, and the cam are dispersed at positions not overlapping with one another on the rotation flat plane.

7. The micropump according to claim 1, further comprising a speed reduction mechanism or a speed increase mechanism between the rotor and the cam.

8. The micropump according to claim 1, wherein the tube guide frame has a tube guide groove into which the tube is inserted, and a tube holding portion which holds the tube in the tube guide groove.

9. The micropump according to claim 1, wherein a guide portion which locates the center of the circular-arc-shaped part of the tube and a rotation center of the cam at the same position at the time of attachment of the tube unit to the control unit is provided on each side surface of the tube unit and the control unit.

10. The micropump according to claim 9, wherein a detection unit which detects that the center of the circular-arc shape of the tube and a rotation center of the cam are located at the same position at the time of attachment of the tube unit to the control unit is provided between the tube unit and the control unit.

11. The micropump according to claim 1, further comprising:
    a cover member for fixing the tube unit to the control unit; and
    an elastic member which biases the tube unit to the control unit such that the center of the circular-arc shape of the tube and a rotation center of the cam can be located at the same position provided between the cover member and the tube unit.

12. The micropump according to claim 11, wherein a biasing force of the elastic member is larger than a tube pressing force of the plurality of fingers.

13. The micropump according to claim 1, further comprising:
    a tube regulating wall which regulates shift of the tube caused by the press of the plurality of fingers; and
    an elastic member disposed between the tube and the tube regulating wall.

14. The micropump according to claim 1, wherein a part or an entire area of outer peripheries of the tube unit and the control unit is transparent.

15. The micropump according to claim 1, wherein either one or both of the power source and the reservoir are accommodated in the tube unit.

16. The micropump according to claim 15, wherein the power source and the reservoir are attachable to and detachable from the tube unit.

17. The micropump according to claim 1, wherein the reservoir has a port for introducing fluid into the reservoir or sealing the reservoir.

18. The micropump according to claim 1, further comprising an air vent filter which blocks passage of bubbles at a communicating portion between the reservoir and the tube.

* * * * *